US009040062B2

(12) United States Patent
Maeda et al.

(10) Patent No.: US 9,040,062 B2
(45) Date of Patent: May 26, 2015

(54) PREPARATION FOR TREATMENT OF SPINAL CORD INJURY

(75) Inventors: Miho Maeda, Suita (JP); Akiyoshi Kishino, Osaka (JP); Akihiko Sano, Nakano-ku (JP); Hideyuki Okano, Shinjuku-ku (JP); Masaya Nakamura, Shinjuku-ku (JP); Liang Zhang, Shinjuku-ku (JP)

(73) Assignees: SUMITOMO DAINIPPON PHARMA CO., LTD., Osaka (JP); KEIO UNIVERSITY, Tokyo (JP)

( * ) Notice: Subject to any disclaimer, the term of this patent is extended or adjusted under 35 U.S.C. 154(b) by 0 days.

(21) Appl. No.: 13/814,341

(22) PCT Filed: Aug. 4, 2011

(86) PCT No.: PCT/JP2011/067838
§ 371 (c)(1),
(2), (4) Date: Feb. 5, 2013

(87) PCT Pub. No.: WO2012/018069
PCT Pub. Date: Feb. 9, 2012

(65) Prior Publication Data
US 2013/0142848 A1 Jun. 6, 2013

(30) Foreign Application Priority Data

Aug. 6, 2010 (JP) ................................. 2010-177255

(51) Int. Cl.
| | | |
|---|---|---|
| A61K 9/00 | (2006.01) | |
| A61K 9/70 | (2006.01) | |
| A61K 47/34 | (2006.01) | |
| A61K 31/352 | (2006.01) | |
| A61K 47/28 | (2006.01) | |
| A61K 47/02 | (2006.01) | |
| A61K 47/38 | (2006.01) | |
| A61P 25/00 | (2006.01) | |
| A61P 43/00 | (2006.01) | |

(52) U.S. Cl.
CPC ............ *A61K 9/0024* (2013.01); *A61K 9/0085* (2013.01); *A61K 9/7007* (2013.01); *A61K 31/352* (2013.01); *A61K 47/02* (2013.01); *A61K 47/28* (2013.01); *A61K 47/34* (2013.01); *A61K 47/38* (2013.01)

(58) Field of Classification Search
CPC ... A61K 9/0024; A61K 9/7007; A61K 47/28; A61K 47/02; A61K 9/0085; A61K 47/38; A61K 31/352; A61K 47/34
See application file for complete search history.

(56) References Cited

U.S. PATENT DOCUMENTS

| | | |
|---|---|---|
| 4,191,741 A | 3/1980 | Hudson et al. |
| 4,331,651 A | 5/1982 | Reul et al. |
| 4,985,253 A | 1/1991 | Fujioka et al. |
| 5,480,653 A | 1/1996 | Aguadisch et al. |
| 5,851,547 A | 12/1998 | Fujioka et al. |
| 6,756,048 B1 | 6/2004 | Sano et al. |
| 2003/0166711 A1 | 9/2003 | Kimura et al. |
| 2007/0105948 A1 | 5/2007 | Ikeda et al. |
| 2008/0199491 A1 | 8/2008 | Brandon et al. |
| 2009/0264491 A1* | 10/2009 | McKay et al. ................ 514/401 |
| 2010/0081617 A1 | 4/2010 | Okano et al. |

FOREIGN PATENT DOCUMENTS

| | | |
|---|---|---|
| JP | 55-45694 | 3/1980 |
| JP | 62-174007 | 7/1987 |
| JP | 3-151322 | 6/1991 |
| JP | 7-187994 | 7/1995 |
| JP | 2009-114085 | 5/2009 |
| WO | 00/15199 | 3/2000 |
| WO | 02/09756 | 2/2002 |
| WO | 2005/053678 | 6/2005 |
| WO | 2008/105088 | 9/2008 |

OTHER PUBLICATIONS

Soulas et al., Journal of Applied Polymer Science, 113: 936-949 (2009).*
Shin Etsu, Low-Substituted Hydroxypropyl Cellulose NF, pp. 1-23 (2006) (downloaded from http://www.elementoorganika.ru/files/lhpc.pdf, Mar. 20, 2014).*
Soulas et al., Journal of Applied Polymer Science, 120: 821-830 (2011).*
International Search Report issued Aug. 30, 2011 in International (PCT) Application No. PCT/JP2011/067838.
Y. Luo et al., "Collapsin: A Protein in Brain That Induces the Collapse and Paralysis of Neuronal Growth Cones", Cell, vol. 75, Oct. 22, 1993, pp. 217-227.
A. Kolodkin et al., "The *semaphorin* Genes Encode a Family of Transmembrane and Secreted Growth Cone Guidance Molecules", Cell, vol. 75, pp. 1389-1399, Dec. 31, 1993.

(Continued)

*Primary Examiner* — Kortney L Klinkel
*Assistant Examiner* — Lisbeth C Robinson
(74) *Attorney, Agent, or Firm* — Wenderoth, Lind & Ponack, L.L.P.

(57) ABSTRACT

The present invention is a solid sustained-release formulation comprising an agent for inhibiting semaphorin 3A as an active ingredient, which comprises an agent for inhibiting semaphorin 3A and pharmaceutically acceptable hardly water-soluble solid substance, in which the carrier is silicone.

17 Claims, 15 Drawing Sheets

(56) References Cited

OTHER PUBLICATIONS

S. Kaneko et al., "A selective Sema3A inhibitor enhances regenerative responses and functional recovery of the injured spinal cord", Nature Medicine, vol. 12, No. 12, pp. 1380-1389, Dec. 2006.

K. Fujioka et al., "Protein release from collagen matrices", Advanced Drug Delivery Reviews, vol. 31, pp. 247-266, 1998.

* cited by examiner

Exposure of rat's spinal cord at T8

Placement of silicone formulation

Spinal cord treated with placebo sheet

Spinal cord treated with the drug-containing sheet

Pathological section of the spinal cord treated with the drug-containing sheet

* P<0.05
** P<0.01
(one-way ANOVA and Bonferroni post hoc analysis)

Control

Formulation 5

Control    Formulation 5    Formulation 5 + rehabilitation

PREPARATION FOR TREATMENT OF SPINAL CORD INJURY

TECHNICAL FIELD

The present invention provides a medicament for locally treating spinal cord injury, which comprises a compound of after-mentioned Formula (1) or a pharmaceutically acceptable salt thereof as an active ingredient which has the activity for inhibiting semaphorin 3A. Namely, the present invention is directed to a solid controlled-release formulation using a biocompatible polymer as a carrier, which is suitable for the implant in the vicinity of spinal cord injury site, and which can deliver an agent for inhibiting semaphorin 3A to a damaged site effectively over a long time which is required to treat spinal cord injury. In detail, the formulation of the present invention can be implanted in subdural space in the vicinity of a damaged spinal cord and deliver an active ingredient to the damaged site effectively over about one month which is needed for neuroregeneration to exert the efficacy of the active ingredient.

BACKGROUND ART

Neuron is an atypical cell in biological body, which has no ability to divide. Thereby, once a neuron is damaged, it is known that the nerve function is not recovered for a long time. Particularly in the central nervous system such as brain and spinal cord, it is known that a damaged nerve fiber therein is hardly regenerated. It is considered to be caused by a substance for inhibiting the nerve growth which exists in the central nervous system. Actually, some neuroregeneration inhibitory factors such as Nogo and MAG have been discovered. In addition, it has been discovered that chondroitin sulfate proteoglycan has a similar action. And, semaphorin is also one of such inhibitory factors of nerve growth.

Semaphorins are endogenous proteins which are identified as a factor that can retract the nerve growth cone and suppress the axonal growth. Until now, about 20 kinds of molecular species thereof have been known. Amongst them, semaphorin 3A has been studied the most (see, Non-Patent References 1 and 2), which is known to have in vitro potent activities for inhibiting neurite outgrowth and retracting growth cone. This protein can induce the growth cone retraction in cultural neuron, in a low concentration of 10 pM and in a short time. As a compound for inhibiting the action of semaphorin 3A (i.e., semaphorin inhibitor), it has been known that a certain group of xanthone compounds has the action for inhibiting semaphorins and the action for promoting neuroregeneration (see, Patent References 1 and 2).

Patent References 1 and 2 disclose xanthone compounds represented by the compounds of the after-mentioned Formula (1), processes for preparing the compounds, and the action for inhibiting semaphorins thereof. As for formulations comprising the compound, however, Patent Reference 1 merely describes a general explanation about formulation technologies, and Patent Reference 2 discloses only an eye drop and an ophthalmic ointment comprising the compound in Examples 4 to 7, but neither discloses nor suggests any practical formulations comprising the compound of the after-mentioned Formula (1) for treating spinal cord injury.

In spinal cord injury which is a degenerative disease of the central nervous system, since the central nerve fiber in spinal cord is damaged, in most cases neurologic dysfunction cannot be drastically recovered. Since the above-mentioned inhibitory factors of nerve growth were discovered, many studies for treating spinal cord injury by inhibiting the action of these factors have been done. *Kaneko*, et al. found that a lot of semaphorin 3A appeared in the nerve tissue after spinal cord was damaged, and then supposed that semaphorin 3A inhibited the regeneration of spinal cord nerve. Then, they prepared a rat spinal cord injury model, to which the above semaphorin inhibitor was intrathecally administered in a sustained manner, and monitored the change of motor function. As a result, the nerve fiber in spinal cord of the rats given the semaphorin inhibitor re-enlongated, and thereby the motor function was also recovered. This experimental result suggested that a semaphorin inhibitor could be a useful agent for treating spinal cord injury (e.g. Non-Patent Reference 3).

It is considered that the inhibitory factors of nerve growth continue to act for a long time in spinal cord injury. Accordingly, in order to suppress the action of these factors with the drug and promote the enlongation of nerve fiber, it is necessary to continue to administer the drug for a long time. And, the transport of a substance from blood to the spinal cord, as well as the brain, is highly regulated by blood-brain barrier. Accordingly, in order to make the action of the drug compound enough effective in spinal cord, the intrathecal administration is generally conducted.

Until now, in order to continuously administer a semaphorin inhibitor into spinal cavity, it is necessary to repeat the administration by injection to spinal cavity, or place the tip of a catheter in spinal cavity and then continuously administer an aqueous solution of a semaphorin inhibitor via the catheter. However, these administration methods might bring down an infection or damage nerve fiber, thus patients given such treatment are supposed to have severe physical burden.

As a new method to solve the problem, a novel technology of formulating a semaphorin inhibitor into a sustained-release formulation for a local treatment is expected to reduce the frequency of administration, retain a necessary concentration in the target site to exert the action of the drug, and reduce side effects.

As for an implantable sustained-release formulation, the technology in which a polymer material is used as a carrier for drug has been actively researched/developed, and some trials of the sustained release of a protein drug using hydrophilic polymer collagen as a carrier have been already reported (e.g. Non-Patent Reference 4). Collagen is a biocompatible carrier suitable for the sustained release of a water-soluble polymer such as protein, but the releasable period is only about one week for protein. For a low molecular water-soluble drug, the releasable period thereof is shorter, thus collagen is not suitable for the long-time sustained release of low molecular drugs.

In order to achieve the long-time sustained release profile, hydrophilic polymers such as collagen and polysaccharide are not adequate as a carrier, but hydrophobic polymers are useful. Typical hydrophobic polymers having good biocompatibility include silicone.

Norplant™ is a capsule preparation wherein powdery levonorgestrel as an active ingredient is encapsulated in a cylindroid silicone container, which is characterized by continuing to release levonorgestrel in vivo for 5 years. And, as an example of matrix formulations, Compudose™ has a form wherein estradiol as an active ingredient is dispersed in silicone (e.g. Patent Reference 3).

Both the active ingredients in Norplant and Compudose are a lipophilic drug, which can be dissolved/diffused in silicone that is a hydrophobic polymer. Thereby, the drug on the surface of the formulation is spread to the surrounding tissues, and then the drug included in higher concentration inside the formulation is transferred by diffusion to the lower-concentrated surface of the formulation because the concentration of the lipophilic drug on the surface of the formulation decreases. Thus, the sustained release becomes possible.

However, water-soluble compounds such as the compound of Formula (1) which is an active ingredient of the present invention are hardly soluble in a hydrophobic polymer carrier, and do not autonomously diffused/released therein. Hence, another release mechanism which is quite different from that of lipophilic drug is supposed to be necessary for such water-soluble compounds.

One of general methods for releasing a water-soluble drug out of a hydrophobic polymer carrier is a release of the drug from pores of a reservoir-type formulation. Besides, there is another releasing mechanism wherein a drug is dispersed in a carrier, in which firstly a drug particle in close proximity to the surface of the formulation is eluted out by water in the surrounding tissues, and then another drug particle adjacent to the dissolved particle is eluted to the surface, that is, the phenomenon is sequentially repeated to form a continuing water channel system, and the drug is diffused in the channel while releasing the drug. Then, the difference in osmotic pressure produced inside the formulation can also make the inside of the formulation cracked to facilitate forming the channel and further can increase the release by the extruding effect of the swelling. Accordingly, it is necessary that each particle in a carrier lies adjacent to each other or the difference in osmotic pressure is produced inside the formulation, in order to continue the release. Thus, the mechanism is characterized by comprising more than a certain amount of a water-soluble drug or a water-soluble additive agent. As an example thereof, Patent Reference 4 discloses a method of controlling the release of a drug out of a silicone carrier by adding albumin.

However, such release system of a water-soluble drug is very difficult to control the release, i.e., in general, the initial release speed thereof is too fast and the drug is supposed to be explosively released, and then the release amount of the drug decreases over time like first-order release profile. After all, such release system is difficult to control the constant and steady release for a long time.

It is sometimes useful for a patient that the initial release speed is fast, but generally there are some problems, for example, side effects can happen due to such rapid increase of initial drug concentration, or the decrease of the drug release over time makes the use difficult. In particular, the initial release speed tends to be faster as the surface area is larger, hence, for a small formulation or a thin sheet-like formulation whose surface area is large per its weight, it is difficult to control the release while suppressing the initial burst. Thus, for such release system, it is difficult to try to miniaturize a formulation or reduce the thickness of a formulation for its purpose.

Patent Reference 5 discloses a technology that a water-soluble drug is sustainably released at a constant rate out of a hydrophobic polymer carrier, i.e., a columnar formulation wherein only the surround of a layer comprising a water-soluble drug is coated with an outer layer which can protect water and control the swelling of the inner layer. However, the technology has a disadvantage that it is impossible to miniaturize a formulation or formulate a thin film product. In addition, the drug-release surface thereof is only cross-section surfaces which are not coated with the outer layer, thereby the drug is localized around the cross-section surfaces in high concentration. Thus, the technology is not suitable for delivering a drug uniformly to the desired area.

Patent Reference 6 discloses a dressing that can release a drug sustainably, wherein a hydrophilic ingredient is used as an ingredient for controlling the drug release out of silicone carrier. The mechanism of releasing a drug is that firstly the hydrophilic ingredient becomes in hyperosmotic state, thereby the formulation is expanded, followed by the contraction of the silicone polymer to release the drug. However, such technology is substantially impracticable since the formulation can be expanded in an environment where water exists in the vicinity and then the volume of the formulation can be severely increased to compress the surrounding tissue when the formulation is used in vivo. Furthermore, the release speed of such formulation is fast, thus the release is expected to be only for several hours to several days, i.e., unsuitable for long-term sustained release. In addition, Patent Reference 6 teaches that preferred hydrophilic ingredients are liquid, and the most preferred hydrophilic ingredient is glycerol, and also exemplifies some liquid ingredients such as liquid polyethylene glycol, but these ingredients inhibit the shape-forming/curing of silicone, thus it is unsuitable to comprise such ingredients in the solid silicone formulations mentioned below.

In addition, Patent Reference 7 discloses a sustained-release formulation for a lipophilic drug wherein a water-soluble substance is dispersed in a water-imperviable biocompatible material such as silicone.

As mentioned above, in order to put a semaphorin 3A inhibitor to clinically practical use as a drug for treating spinal cord injury, a decent delivery technology is essential. However, there had not been found any practical sustained-release formulations suitable for a local administration of the compound of Formula (1).

PRIOR ART

Patent Reference

[Patent Reference 1] WO 2002/009756
[Patent Reference 2] WO 2005/053678
[Patent Reference 3] JP 55-45694 A
[Patent Reference 4] JP 62-174007 A
[Patent Reference 5] JP 7-187994 A
[Patent Reference 6] JP 3-151322 A
[Patent Reference 7] WO 2000/015199

Non-Patent Reference

[Non-Patent Reference 1] Cell, Volume 75, p 217, 1993
[Non-Patent Reference 2] Cell, Volume 75, p 1389, 1993
[Non-Patent Reference 3] Nature Medicine, Volume 12, p 1380, 2006
[Non-Patent Reference 4] Advanced Drug Delivery Reviews, Volume 31, p 247, 1998

SUMMARY OF INVENTION

Problem to be Solved by the Invention

The purpose of the present invention is to provide a useful and practical sustained-release formulation comprising a semaphorin inhibitor as an active ingredient which is suitable for local treatment of spinal cord injury.

Means to Solve the Problem

The present inventors supposed that in order to enough exert the effect of the compound of Formula (1) or a pharmaceutically acceptable salt thereof which is a semaphorin inhibitor for treating spinal cord injury, it is necessary to keep an effective concentration of the compound to inhibit semaphorin 3A in the tissue for a long time required for neuroregeneration. Based on the supposition, the present inventors have extensively studied and then have found that a formulation of the compound of Formula (1) comprising a hydrophobic polymer as a carrier, and a hardly water-soluble substance such as low substituted hydroxypropylcellulose and cholesterol as an additive agent can make it possible to release the compound for a long time of 2 or more weeks to achieve an adequate effect on neuroregeneration. In addition, the present inventors have also succeeded in preparing a practical drug product for clinically treating spinal cord injury, which has an implantable form that does not damage the neuron through physical stress. Based upon the new findings, the present invention has been completed.

The present invention provides inventions of various embodiments described below.

Term 1. A sustained-release formulation having a solid sheet-like or rod-like shape which comprises the compound of Formula (1):

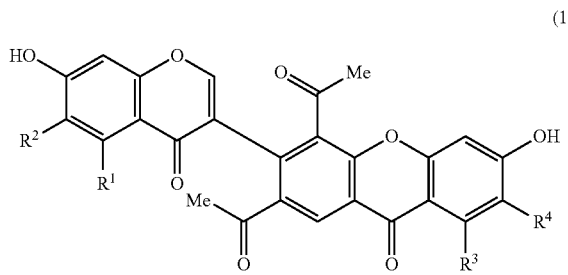

(1)

wherein $R^1$ is hydrogen atom or carboxyl group, $R^2$ is hydrogen atom or hydroxyl group, $R^3$ is hydrogen atom or carboxyl group, and $R^4$ is hydrogen atom or hydroxyl group, or a pharmaceutically acceptable salt thereof, and a hardly water-soluble substance, in which the carrier is a biocompatible hydrophobic polymer, wherein the hardly water-soluble substance is low substituted hydroxypropylcellulose, partly pregelatinized starch, crospovidone, croscarmellose sodium, carmellose calcium, sodium carboxymethyl starch, hydroxypropyl starch, myristic acid, lauric acid, palmitic acid, saccharin and/or cholesterol.

Term 2. The sustained-release formulation of Term 1 wherein the hardly water-soluble substance is low substituted hydroxypropylcellulose, partly pregelatinized starch, crospovidone, croscarmellose sodium, myristic acid, saccharin and/or cholesterol.

Term 3. The sustained-release formulation of Term 1 wherein the hardly water-soluble substance is low substituted hydroxypropylcellulose and/or cholesterol.

Term 4. The sustained-release formulation of any one of Terms 1 to 3 wherein the solid sustained-release formulation has a shape suitable for the placement in the vicinity of spinal cord injury site or in spinal cavity.

Term 5. The sustained-release formulation of any one of Terms 1 to 4 wherein the biocompatible hydrophobic polymer is silicone.

Term 6. The sustained-release formulation of any one of Terms 1 to 5 wherein the solid sustained-release formulation has a sheet-like shape whose thickness is 0.1 to 1.5 mm.

Term 7. The sustained-release formulation of any one of Terms 1 to 6 wherein the hardly water-soluble substance is contained in 3 to 35% by weight per the whole weight of the formulation.

Term 8. The sustained-release formulation of any one of Terms 1 to 7 which contains silicone in 55% or more by weight per the whole weight of the formulation.

Term 9. The sustained-release formulation of any one of Terms 1 to 8 further comprising a water-soluble additive agent.

Term 10. The sustained-release formulation of Term 9 wherein the water-soluble additive agent is sodium chloride, glucose, mannitol, lactose, glycine, sodium cholate, sodium glycocholate and/or sodium desoxycholate.

Term 11. The sustained-release formulation of Term 9 wherein the water-soluble additive agent is sodium chloride and/or sodium desoxycholate.

Term 12. The sustained-release formulation of Term 11 wherein the hardly water-soluble substance is low substituted hydroxypropylcellulose, and the water-soluble additive agent is sodium chloride.

Term 13. The sustained-release formulation of Term 11 wherein the hardly water-soluble substance is cholesterol, and the water-soluble additive agent is sodium desoxycholate.

Term 14. The sustained-release formulation of Term 11 wherein the hardly water-soluble substance is cholesterol, and the water-soluble additive agent is sodium chloride and sodium desoxycholate.

Term 15. The sustained-release formulation of any one of Terms 1 to 14 wherein the total weight of
(i) the compound of Formula (1) or a pharmaceutically acceptable salt thereof,
(ii) low substituted hydroxypropylcellulose, partly pregelatinized starch, crospovidone, croscarmellose sodium, carmellose calcium, sodium carboxymethyl starch, hydroxypropyl starch, myristic acid, lauric acid, palmitic acid, saccharin or cholesterol, and
(iii) the optional water-soluble additive agent is in 10 to 40% per the whole weight of the formulation, provided that the total weight of the compound of Formula (1) or a pharmaceutically acceptable salt thereof and the water-soluble additive agent is not more than 35% per the whole weight of the formulation.

Term 16. The sustained-release formulation of any one of Terms 1 to 15 comprising essentially the compound of Formula (1) or a pharmaceutically acceptable salt thereof, hardly water-soluble substance, and an optional water-soluble additive agent, and which comprises a biocompatible hydrophobic polymer as a carrier.

Term 17. The sustained-release formulation of any one of Terms 1 to 16 wherein the compound of Formula (1) or a pharmaceutically acceptable salt thereof is contained in an amount of 3 to 350 μg per 1 mg of the formulation.

Term 18. The sustained-release formulation of any one of Terms 1 to 17 which is a matrix formulation.

Term 19. The sustained-release formulation of any one of Terms 1 to 18 wherein $R^1$ and $R^3$ are carboxyl group, and $R^2$ and $R^4$ are hydroxyl group.

Term 20. A method for treating spinal cord injury using the sustained-release formulation of any one of Terms 1 to 19.

Term 21. The method of Term 20 which is combined with another method for treating spinal cord injury.

Term 22. The method of Term 20 or 21 which is further combined with rehabilitation.

DESCRIPTION OF EMBODIMENTS

Figure 1:
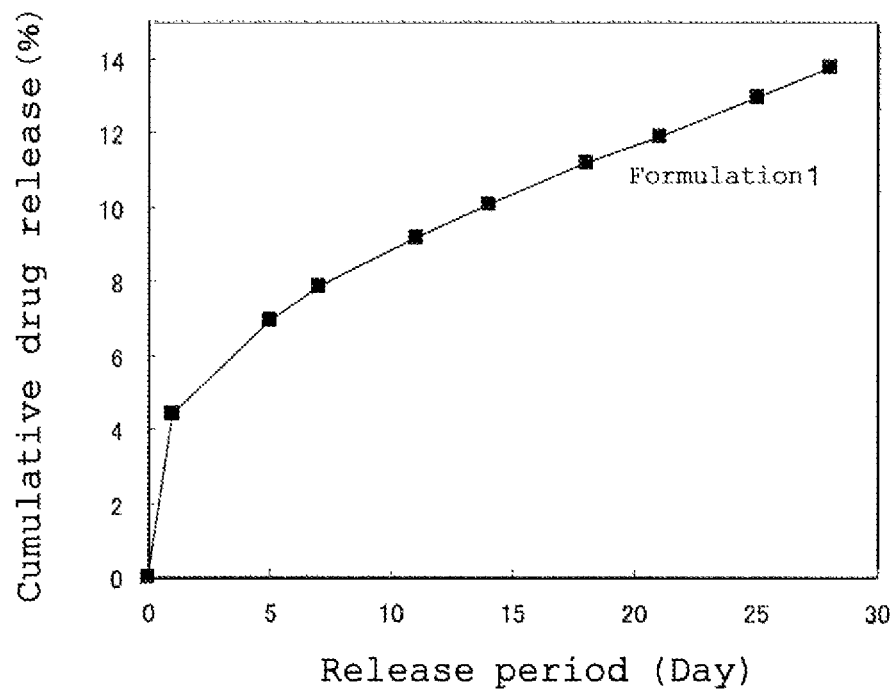
FIG. 1 Results of Test Example 1 are shown.

The compound of Formula (1) used herein is a water-soluble drug which is known to have a semaphorin 3A inhibitory activity. The compound of Formula (1), which includes vinaxanthone (also known as "SPF-3059-5"; see, the following formula) used in the following Examples, can be prepared on the basis of Patent Reference 1 (see, pages 42 to 47, Example 1) and JP 2008-013530 A (see, pages 26 to 27, Example 3).

Vinaxanthone

The hardly water-soluble solid substance used herein includes a medically/pharmaceutically acceptable substance which is solid at room temperature and slightly soluble in an in vivo environment (i.e. at a neutral pH and 37° C.). In specific, the hardly water-soluble solid substance includes, for example, swellable polymers used as a disintegrant for an oral preparation (e.g. low substituted hydroxypropylcellulose, partly pregelatinized starch, crospovidone, croscarmellose sodium, carmellose calcium, sodium carboxymethyl starch, and hydroxypropyl starch); fatty acids which are solid at room temperature (e.g. myristic acid, lauric acid and palmitic acid); saccharin; and cholesterol, which may be used alone or as a mixture. The low substituted hydroxypropylcellulose used herein contains 5 to 16% of hydroxypropoxyl group. The hardly water-soluble substance is preferably low substituted hydroxypropylcellulose, partly pregelatinized starch, crospovidone, croscarmellose sodium, myristic acid, saccharin and/or cholesterol; and the most preferably low substituted hydroxypropylcellulose and/or cholesterol. The cholesterol can be used together with a substance which helps the dissolution thereof (e.g. bile salt) to achieve further preferred effects.

The present invention may comprise a water-soluble additive agent in order to, for example, optimize the release rate or stabilize the drug. The water-soluble additive agent used herein is not limited as long as it is solid at room temperature and medically/pharmaceutically acceptable; and includes preferably non-primary-amine-containing saccharides, salts and bile salts. In specific, the saccharides used herein include, for example, glucose, mannitol, lactose, trehalose, sucrose, erythritol, sorbitol and xylitol; and preferably glucose, mannitol and lactose. The salts used herein include, for example, sodium chloride, potassium chloride and calcium chloride; and preferably sodium chloride. The bile salts used herein include, for example, primary bile salts such as sodium cholate and sodium chenodeoxy cholate, secondary bile salts such as sodium desoxycholate and sodium lithocholate, and conjugated bile salts such as sodium glycocholate and sodium taurocholate; and preferably sodium cholate, sodium desoxycholate and sodium glycocholate. More preferably, the water-soluble additive agent is sodium chloride and/or sodium desoxycholate. One or several different types of the above-listed water-soluble additive agents may be contained in the solid formulation of the present invention.

The most preferred water-soluble additive agent is sodium desoxycholate.

In case that low substituted hydroxypropylcellulose is used as the hardly water-soluble substance, an excellent controlled-release can be attained by combining sodium chloride as the water-soluble additive agent. In case that cholesterol is used as the hardly water-soluble substance, it is preferable to combine a substance which helps the dissolution thereof, as described above. In specific, cholesterol can be combined with preferably the above-mentioned bile salts; more preferably sodium cholate, sodium desoxycholate or sodium glycocholate; and the most preferably sodium desoxycholate or a mixture of sodium desoxycholate and sodium chloride to attain an excellent controlled-release. In case that sodium desoxycholate and sodium chloride are used in combination, the total content of the sodium desoxycholate and sodium chloride is less than 35%, preferably 20% or less; and the ratio thereof is not specifically limited and can be in any proportion.

Sodium chloride as the water-soluble additive agent exhibits an excellent effect on enhancing the release, but an excess amount thereof produces an excessively great difference in osmotic pressure inside the formulation and thus a remarkable swelling of the formulation may be caused. Accordingly, it is preferable to keep the amount of sodium chloride to 10% or less.

The hydrophobic polymer used as the carrier is not specifically limited as long as it is biocompatible, and includes preferably carriers which do not contain primary amines. It is because the compound of Formula (1), in particular vinaxanthone (also known as "SPF-3059-5"), easily reacts with primary amines, while it is important to keep the compound stable inside the formulation to attain a sustained-release for a long period of 1 month or more. In case of preparing a film-like formulation, it is preferable that the formulation has a suitable intensity and flexibility.

The hydrophobic polymer is broadly classified into non-biodegradable polymers and biodegradable polymers, either of which can be used herein, and they should not be limited to the following examples. The non-biodegradable polymers include, for example, silicone and polyurethane. The biodegradable polymers include, for example, polylactic acid, polyglycolic acid, polycaprolactone and copolymers thereof.

Among the hydrophobic polymers, silicone is a further preferred carrier. Silicone shows an excellent biocompatibility and has been successfully used as a material for artificial organs and medical devices for a long time. Silicone can exist in various states such as oil, gel and rubber, depending on the polymerization degree of siloxane bonds and substituents induced in the silicone. The silicone used herein is not specifically limited as long as it is a solid, and such a solid may be made by curing oil-state or gel-state silicone. The silicone used herein may be, for example, SILASTIC Q7-4750 of polydimethylsiloxane (manufactured by Dow Corning Corp.) and MED-4750 (manufactured by Nusil Corp.).

The matrix formulation used herein means a solid controlled-release formulation wherein the powder pharmaceuticals and/or additives are homogeneously dispersed in the hydrophobic carrier.

The shape of the solid formulation used herein is not specifically limited as long as the shape is suitable for the placement in the vicinity of spinal cord injury site or in spinal cavity.

The "shape possible for the placement in the vicinity of spinal cord injury site or in spinal cavity" used herein means a shape which does not compress the spinal nerve after the placing, and includes preferably sheet-like and cylindroid (i.e. rod-like) shapes.

An administration method of the present formulation for the local treatment of spinal cord injury includes inserting the sheet-like formulation to subdural space in the vicinity of the injured site, or attaching the sheet-like formulation to artificial dura mater or setting the sheet-like formulation in place of artificial dura mater to maintain the effective concentration at the injured local-site by surgery; or placing the rod-like formulation in the space of spinal cavity such as cauda equina to maintain the effective concentration in spinal fluid by surgery.

Among the above-shown methods, the sheet-like formulation is suitable for acting on the injured site in a more direct manner; and in order to avoid compressing the nerves or make it possible to use the formulation in a similar manner as an artificial dura mater, the sheet formulation has a thickness of preferably 0.1 to 1.5 mm, more preferably 0.1 to 1 mm, even more preferably 0.23 to 0.5 mm, and when applying to human beings, the most preferable thickness is 0.3 to 0.35 mm. The sheet formulation has a width of 3 to 90 mm and a length of 3 to 140 mm, which may be cut depending on the size of the injured site when use.

Furthermore, the rod-like solid formulation used herein is in a dosage form suitable for placing in spinal cavity; and more specifically, it is a cylindroid formulation with a diameter of 0.3 to 5 mm, more preferably 0.35 to 3 mm, which is suitable for placing in cauda equina with administering devices such as an indwelling needle.

In an experimental manufacture on a small scale, the thickness of the sheet-like formulation or the diameter of the rod-like formulation used herein can be measured after the silicone curing with, for example, calipers, but silicone has elasticity and thus it is necessary to take care that the silicone does not contract/deform by excess compression. Measurements which are less affected by compression may be carried out with, for example, a microscope or an ultrasonic thickness gauge. In a manufacturing process, the thickness/diameter can be measured either before the silicone curing (i.e. immediately after the shape forming) or after the silicone curing; but before curing, silicone is easily deformed by compression and thus extra care is necessary. In addition, it is also possible to make the formulation by predicting the size of the final product on the basis of a preliminary calculation of the size of die used in shape forming (e.g. nozzle, slit, and roller) and the swelling rate at normal pressure.

The "(formulation) comprising essentially the compound of Formula (1) or a pharmaceutically acceptable salt thereof, hardly water-soluble substance, and an optional water-soluble additive agent, and which comprises biocompatible hydrophobic polymer as a carrier" used herein means that the formulation comprises the above-mentioned components as main components, and may also comprise in a small amount some additional components as long as they do not have an adverse impact on the effects of the present formulation. The total weight of "the compound of Formula (1) or a pharmaceutically acceptable salt thereof, hardly water-soluble substance, and an optional water-soluble additive agent, and which comprises biocompatible hydrophobic polymer as a carrier" is 95% or more, for example, 95% or more, 96% or more, 97% or more, 98% or more, 99% or more, and 100% by weight per the whole weight of the formulation. Other than the above-mentioned components, there are basically no components essential for the present formulation, but the formulation may optionally comprise, for example, agents to adjust the curing rate of silicone when manufacturing, substances to adjust the intensity or flexibility of the formulation, and radiopaque markers to identify the place of the implanted formulation by X-ray examination. The radiopaque marker used herein includes, for example, platinum alloys such as platinum, platinum/iridium and platinum/nickel, and palladium alloys.

Without reference to a specific theory, it is perceived that a hardly water-soluble substance is effective in controlling the release of a water-soluble drug from a hydrophobic polymer for the following reason.

As described above, water-soluble drugs are insoluble in hydrophobic polymers and can not be autonomously diffused/released therein; and thus the drug is released through the channel system which is formed by sequence of the drug dissolving from the surface thereof. In channel forming, the conventionally used water-soluble additive agents are rapidly dissolved and voids corresponding to the particle volume of the additive agent are formed inside the formulation, and thus a large channel is suddenly formed in a continuous manner. Accordingly, the release is remarkably accelerated and the formulation shows an initial burst with a short-term release. On the other hand, in case that the formulation comprises a hardly water-soluble solid substance, a large void is not suddenly formed because the rate of dissolution is slow. Thus, the region of the dissolved additive-agent serves as a pathway to deliver a suitable amount of water and water-soluble drug, and it is therefore possible to attain a controlled release for a long period.

The compound of Formula (1) or a pharmaceutically acceptable salt thereof is contained in an amount of 0.3 to 35%, preferably 2 to 20%, and more preferably 8 to 15% by weight per the whole weight of the formulation.

The hydrophobic polymer is contained in an amount of 55% or more, preferably 60 to 90%, more preferably 65 to 85%, and the most preferably 70% by weight per the whole weight of the formulation.

The hardly water-soluble solid substance is contained in an amount of 3 to 35%, preferably 7 to 30%, more preferably 7 to 25% by weight per the whole weight of the formulation. In addition, the low substituted hydroxypropylcellulose is contained in an amount of preferably 7 to 30%, and the most preferably 12 to 25% by weight per the whole weight of the formulation. Furthermore, the cholesterol is contained in an amount of preferably 7 to 20%, and the most preferably 7.5 to 15% by weight per the whole weight of the formulation. A formulation having the above-mentioned contents can accomplish an excellent release for a long period with a small initial burst.

The optional water-soluble additive agent is contained in an amount of less than 35%, preferably 20% or less by weight per the whole weight of the formulation.

The particle size of the drug of Formula (1), hardly water-soluble solid substance and optional water-soluble additive agent, which are dispersed in the carrier as a powder, may have some effects on the release profile. Thus, in order to keep the same quality, it is desirable to optionally control the particle size within a certain range; and typically, the upper limit of the particle size is controlled to 300 μm or less, more preferably 200 μm or less.

The present formulation is useful as a medicament for local treatment of spinal cord injury performed by inhibiting semaphorin 3A, and also shows excellent effects in combination with other therapies used for treating spinal cord injury. For example, the present formulation can be combined with therapies using neuroprotective agents; neurotrophic factors such as FGF-2 (Fibroblast growth factor-2), NGF (Nerve growth factor), BDNF (Brain-derived neurotrophic factor) and HGF (Hepatocyte growth factor) as an enhancer of nerve growth; NBQX (2,3-dioxo-6-nitro-1,2,3,4-tetrahydrobenzo[f]quinoxaline-7-sulfonamide); and the like; and also can be used in combination with cell transplantation. In case that the semaphorin inhibitor and other active ingredients are used in combination, each substance may be designed so that it can be released at a suitable timing (i.e. after a suitable duration) for the treatment. For example, it is desirable that the duration of ingredients used for neuroprotection (e.g. FGF-2 and NBQX) is several days at the beginning, whereas that of ingredients used for nerve regeneration is a longer period of about 1 month. Furthermore, the treatment of the present formulation is safe from catheter-related infection, and thus also shows excellent effects in combination with rehabilitation.

The treatment of spinal cord injury using the sustained-release formulation of the present invention can be combined with rehabilitation generally used for treating patients with spinal cord injury in order to further improve the recovery of neural functions.

EXAMPLES

Hereinafter, the present invention is explained in more detail by illustrating Examples and Comparative Examples, and Test Examples thereof, but the scope of the present invention is not limited thereto.
(Source)
Powder vinaxanthone (which is prepared by cultivating and purifying as described in the reference mentioned above in [0035], or may be chemically synthesized according to K. Tatsuta et al., Chemistry Letters Vol. 36, No. 1 (2007))

L-HPC (Shin-Etsu Chemical Co., Ltd.)
Lactose (Shima Trading Company)
PBS (Takara Bio Inc.)
Crystalline sodium chloride (Nacalai Tesque, Inc.)
Cholesterol (Kanto Chemical Co., Inc.)
Sodium desoxycholate monohydrate (Nacalai Tesque, Inc.)
Glucose (Nacalai Tesque, Inc.)
D-mannitol (Towa-Kasei Co., Ltd.)
PEG4000 (Nacalai Tesque, Inc.)
CMC-Na (Nacalai Tesque, Inc.)
HPC (Nippon Soda Co., Ltd)

Example 1

L-HPC (low substituted hydroxypropylcellulose) (90 mg) and powder vinaxanthone (6 mg) were mixed in a mortar to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 1.

Test Example 1

Formulation 1 prepared in Example 1 was cut into a size of 5 mm×7 mm, put into phosphate buffered saline (PBS) (1 mL), kept at 37° C., measured the vinaxanthone released from the formulation with a high performance liquid chromatograph (UFLC, manufactured by Shimadzu Corporation), and the value was calculated to determine the cumulative percentage of drug release. The results are shown in FIG. 1.

The present formulation, which contains 30% of L-HPC as the hardly water-soluble substance, showed a low initial-burst with less than 5% and attained a sustained-release of a nearly-constant amount during the 4 week release period.

TABLE 1

| | Sheet thickness | Vinaxanthone | L-HPC | Other additive agents |
|---|---|---|---|---|
| Formulation 1 | 0.3 mm | 2 wt % | 30 wt % | None |

Example 2

To lactose (45 mg) were added L-HPC (45 mg) and then powder vinaxanthone (6 mg) in a mortar, and the three kinds of powder were mixed all together to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 2.

Example 3

Crystalline sodium chloride was milled in a mortar to adjust the particle diameter thereof to 100 μm or less, wherein the particle size was measured with a light microscope (phase-contrast microscope BX-51-33-PHU-D, OLYMPAS). To the above-obtained sodium chloride (15 mg) were added L-HPC (75 mg) and then powder vinaxanthone (6 mg), and the three kinds of powder were mixed all together in a mortar to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 3.

Test Example 2

Figure 2:
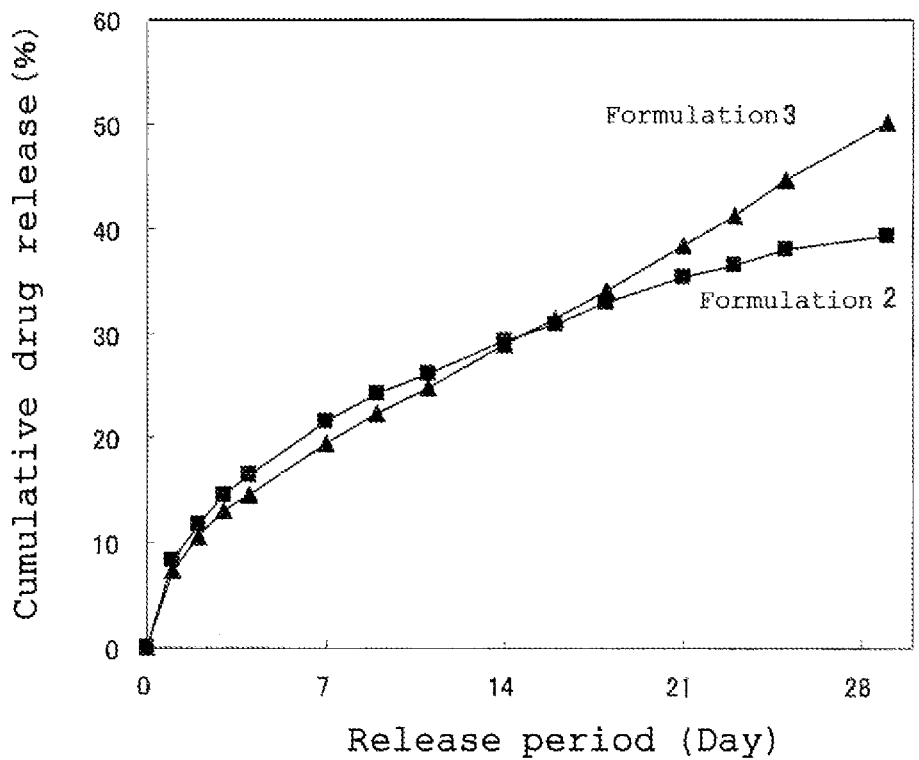
FIG. 2 Results of Test Example 2 are shown.

Each of the formulations prepared in Examples 2 and 3 (see, Table 2) was cut into a size of 5 mm×7 mm, kept at 37° C. in PBS (1 mL), measured the vinaxanthone released from the formulation with a high performance liquid chromatograph, and the value was calculated to determine the cumulative percentage of drug release. The results are shown in FIG. 2.

Formulations 2 and 3 contain L-HPC as the hardly water-soluble substance, and further contain lactose and NaCl respectively as the water-soluble additive agent. Both of the formulations showed a small initial burst, and attained an excellent sustained-release during the 1 month release period.

TABLE 2

| | Sheet thickness | Vinaxanthone | L-HPC | Other additive agents |
|---|---|---|---|---|
| Formulation 2 | 0.3 mm | 2 wt % | 15 wt % | Lactose 15 wt % |
| Formulation 3 | 0.3 mm | 2 wt % | 25 wt % | NaCl 5 wt % |

Example 4

Crystalline sodium chloride was milled in a mortar to adjust the particle diameter thereof to 100 µm or less. To the above-obtained sodium chloride (20 mg) were added L-HPC (100 mg) and then powder vinaxanthone (40 mg), and the three kinds of powder were mixed all together in a mortar to give a mixed powder. SILASTIC Q7-4750 Silicone A component (170 mg) and Silicone B component (170 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 4.

Example 5

Crystalline sodium chloride was milled in a mortar to adjust the particle diameter thereof to 100 µm or less. To the above-obtained sodium chloride (30 mg) were added L-HPC (170 mg) and then powder vinaxanthone (100 mg), and the three kinds of powder were mixed all together in a mortar to give a mixed powder. SILASTIC Q7-4750 Silicone A component (350 mg) and Silicone B component (350 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 5.

Test Example 3

Figure 3:
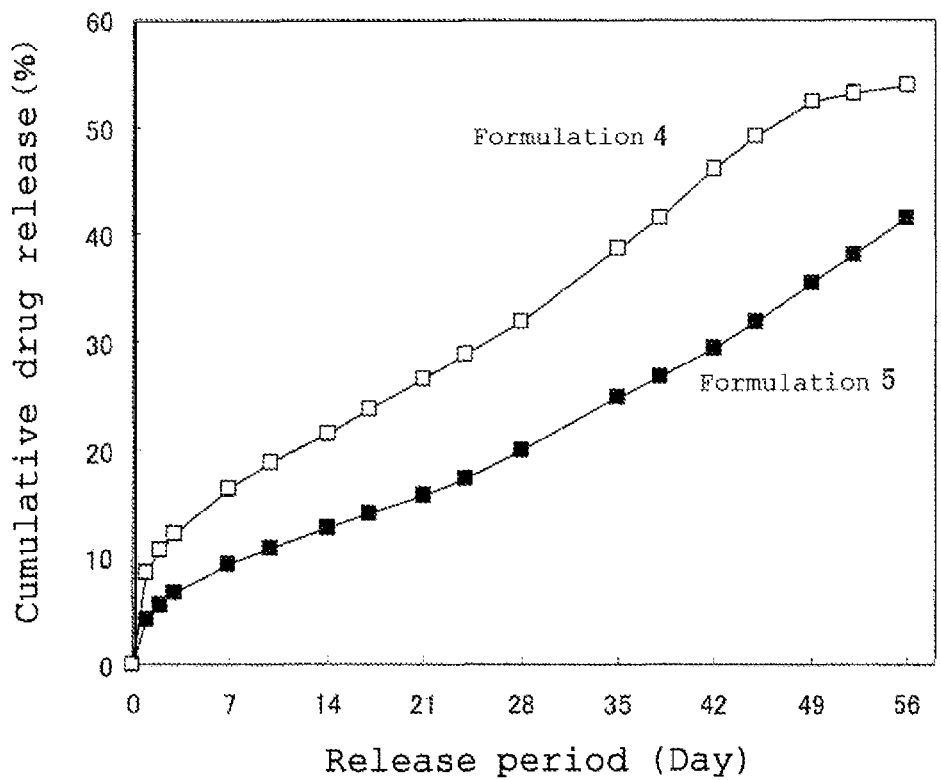
FIG. 3 Results of Test Example 3 are shown.

Each of the formulations prepared in Examples 4 and 5 (see, Table 3) was tested in the same manner as Test Example 1 to determine the cumulative percentage of drug release. The results are shown in FIG. 3.

Formulations 4 and 5, wherein the amount of vinaxanthone is higher than that of the above-shown Formulations 1 to 3, attained an excellent sustained-release for a long period, namely 56 days.

TABLE 3

| | Sheet thickness | Vinaxanthone | L-HPC | Other additive agents |
|---|---|---|---|---|
| Formulation 4 | 0.3 mm | 8 wt % | 20 wt % | NaCl 4 wt % |
| Formulation 5 | 0.3 mm | 10 wt % | 17 wt % | NaCl 3 wt % |

Example 6

Crystalline sodium chloride was milled in a mortar to adjust the particle diameter thereof to 100 µm or less. To the above-obtained sodium chloride (12 mg) were added L-HPC (48 mg) and then powder vinaxanthone (60 mg), and the three kinds of powder were mixed all together in a mortar to give a mixed powder. SILASTIC Q7-4750 Silicone A component (140 mg) and Silicone B component (140 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 6.

Example 7

Crystalline sodium chloride was milled in a mortar to adjust the particle diameter thereof to 100 µm or less. To the above-obtained sodium chloride (12 mg) were added L-HPC (28 mg) and then powder vinaxanthone (80 mg), and the three kinds of powder were mixed all together in a mortar to give a mixed powder. SILASTIC Q7-4750 Silicone A component (140 mg) and Silicone B component (140 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 7.

Test Example 4

Figure 4:
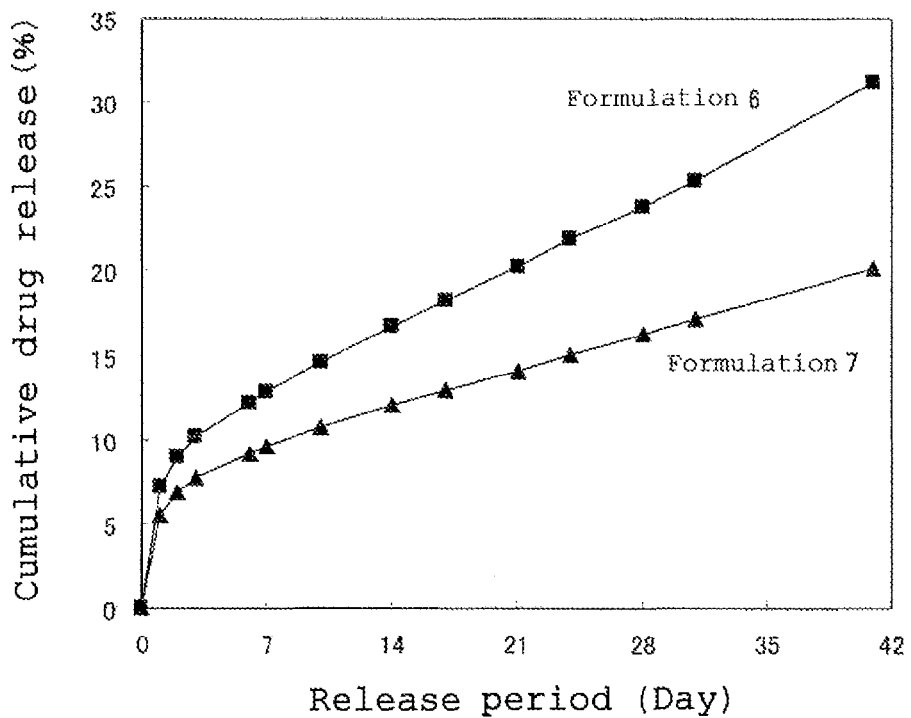
FIG. 4 Results of Test Example 4 are shown.

Each of the formulations prepared in Examples 6 and 7 (see, Table 4) was tested in the same manner as Test Example 1 to determine the cumulative percentage of drug release. The results are shown in FIG. 4.

Formulations 6 and 7, wherein the amount of vinaxanthone is different from that of Formulation 5, attained an excellent sustained-release for a long period, namely 40 days or more.

TABLE 4

|  | Sheet thickness | Vinaxanthone | L-HPC | Other additive agents |
|---|---|---|---|---|
| Formulation 6 | 0.3 mm | 15 wt % | 12 wt % | NaCl 3 wt % |
| Formulation 7 | 0.3 mm | 20 wt % | 7 wt % | NaCl 3 wt % |

Example 8

Crystalline sodium chloride was milled in a mortar to adjust the particle diameter thereof to 100 μm or less. To the above-obtained sodium chloride (18 mg) were added L-HPC (102 mg) and then powder vinaxanthone (60 mg), and the three kinds of powder were mixed all together in a mortar to give a mixed powder. SILASTIC Q7-4750 Silicone A component (210 mg) and Silicone B component (210 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.23 mm. The sheet formulation was cut to give Formulation 8.

Test Example 5

Figure 5:
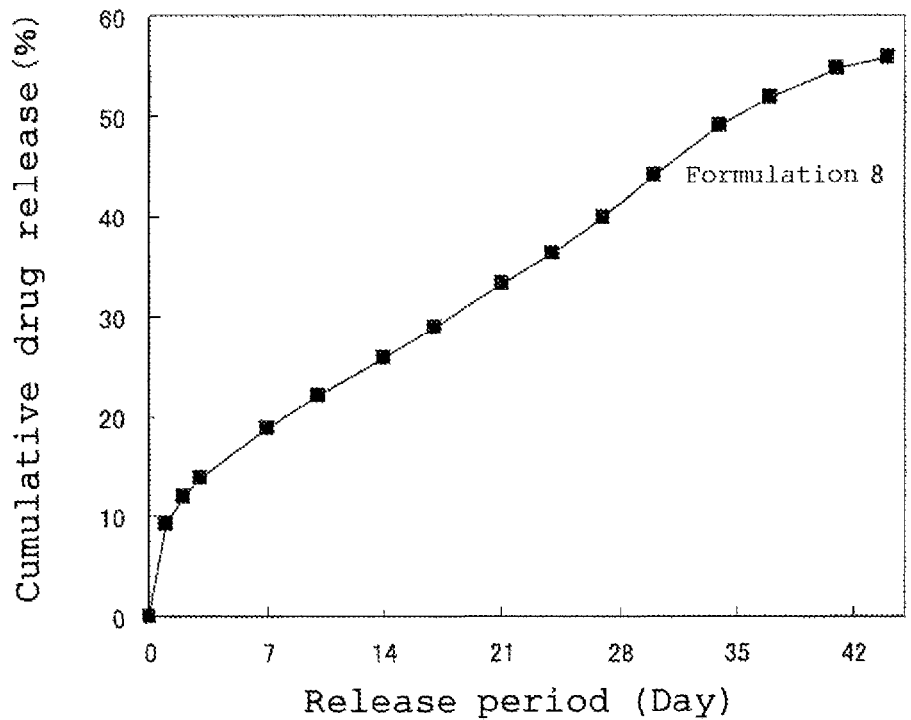
FIG. 5 Results of Test Example 5 are shown.

Formulation 8 prepared in Example 8 was tested in the same manner as Test Example 1 to determine the cumulative percentage of drug release. The results are shown in FIG. 5.

Formulation 8, wherein the thickness of the sheet formulation (0.23 mm) is thinner than that of Formulations 1 to 7 (0.3 mm), attained an excellent sustained-release for a long period, namely 40 days or more.

TABLE 5

|  | Sheet thickness | Vinaxanthone | L-HPC | Other additive agents |
|---|---|---|---|---|
| Formulation 8 | 0.23 mm | 10 wt % | 17 wt % | NaCl 3 wt % |

Example 9

Crystalline sodium chloride was milled in a mortar to adjust the particle diameter thereof to 100 μm or less. To the above-obtained sodium chloride (6 mg) were added sodium desoxycholate dihydrate (17 mg) and cholesterol (17 mg), and then powder vinaxanthone (20 mg), and the four kinds of powder were mixed all together in a mortar to give a mixed powder. SILASTIC Q7-4750 Silicone A component (70 mg) and Silicone B component (70 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 9.

Test Example 6

Figure 6:
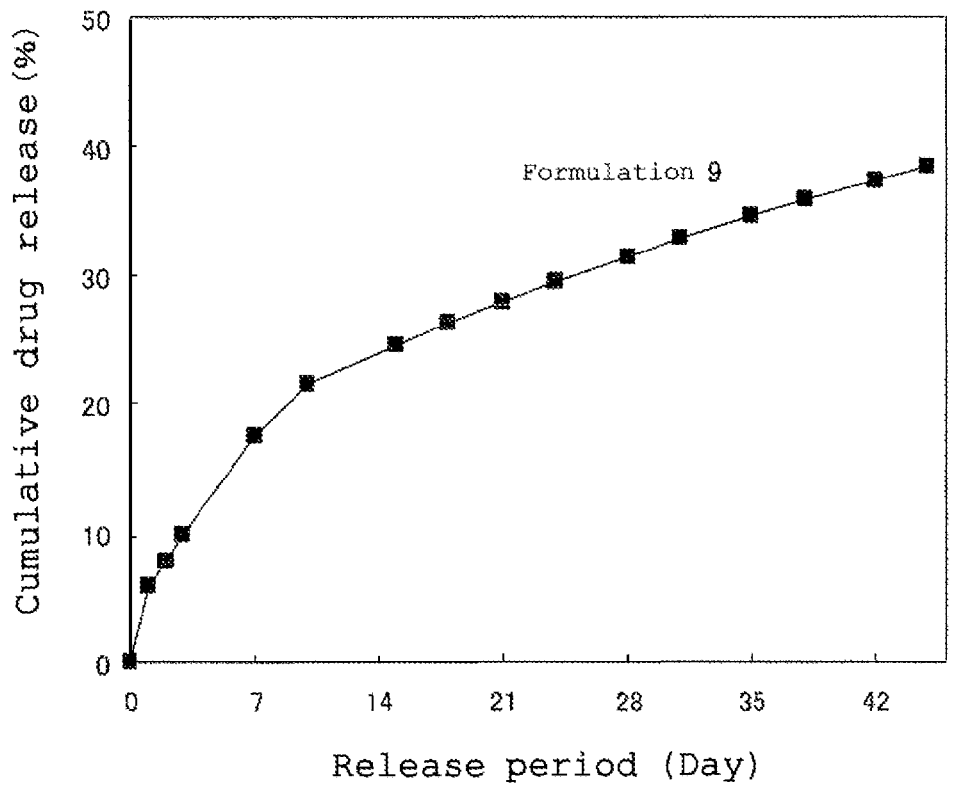
FIG. 6 Results of Test Example 6 are shown.

Formulation 9 prepared in Example 9 was tested in the same manner as Test Example 1 to determine the cumulative percentage of drug release. The results are shown in FIG. 6.

The present formulation, which contains cholesterol as the hardly water-soluble substance and further contains sodium desoxycholate (DC) and NaCl as the water-soluble additive agent, attained an excellent sustained-release for a long period, namely 40 days or more.

TABLE 6

|  | Sheet thickness | Vinaxanthone | Cholesterol | Other additive agents |
|---|---|---|---|---|
| Formulation 9 | 0.3 mm | 10 wt % | 8.5 wt % | DC 8.5 wt % + NaCl 3 wt % |

Example 10

Crystalline sodium chloride was milled in a mortar to adjust the particle diameter thereof to 100 μm or less. To the above-obtained sodium chloride (10 mg) were added sodium desoxycholate dihydrate (15 mg) and cholesterol (15 mg), and then powder vinaxanthone (20 mg), and the four kinds of powder were mixed all together in a mortar to give a mixed powder. SILASTIC Q7-4750 Silicone A component (70 mg) and Silicone B component (70 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 10.

Test Example 7

Figure 7:
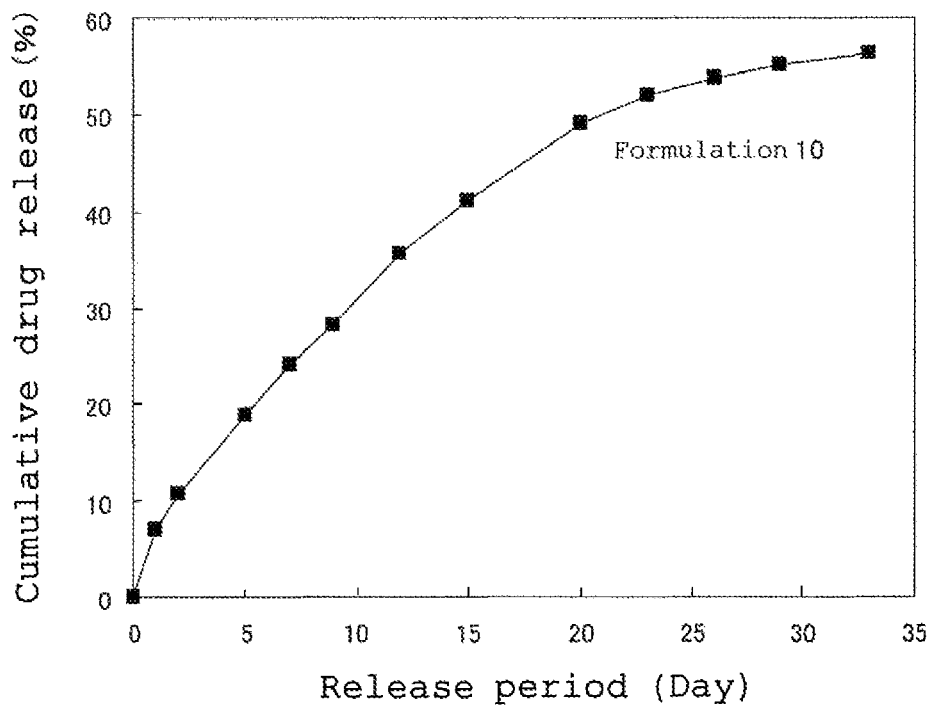
FIG. 7 Results of Test Example 7 are shown.

Formulation 10 prepared in Example 10 was tested in the same manner as Test Example 1 to determine the cumulative percentage of drug release. The results are shown in FIG. 7.

The present formulation, which contains cholesterol as the hardly water-soluble substance and further contains sodium desoxycholate (DC) and NaCl as the water-soluble additive agent, attained an excellent sustained-release for a long period, namely 1 month or more.

TABLE 7

|  | Sheet thickness | Vinaxanthone | Cholesterol | Other additive agents |
|---|---|---|---|---|
| Formulation 10 | 0.3 mm | 10 wt % | 7.5 wt % | DC 7.5 wt % + NaCl 5 wt % |

Example 11

Crystalline sodium chloride was milled in a mortar to adjust the particle diameter thereof to 100 μm or less. To the above-obtained sodium chloride (16 mg) were added cholesterol (24 mg) and then powder vinaxanthone (20 mg), and the three kinds of powder were mixed all together in a mortar to give a mixed powder. SILASTIC Q7-4750 Silicone A component (70 mg) and Silicone B component (70 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 11.

Example 12

Crystalline sodium chloride was milled in a mortar to adjust the particle diameter thereof to 100 μm or less. To the above-obtained sodium chloride (10 mg) were added cholesterol (30 mg) and then powder vinaxanthone (20 mg), and the three kinds of powder were mixed all together in a mortar to give a mixed powder. SILASTIC Q7-4750 Silicone A component (70 mg) and Silicone B component (70 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Formulation 12.

Test Example 8

Figure 8:
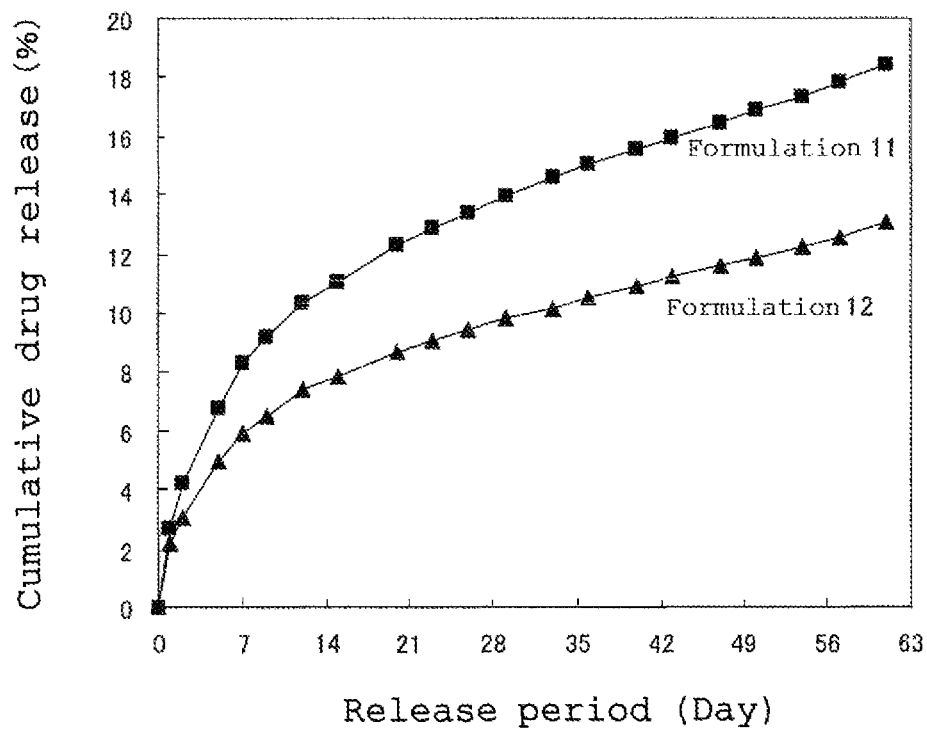
FIG. 8 Results of Test Example 8 are shown.

Each of the formulations prepared in Examples 11 and (see, Table 8) was tested in the same manner as Test Example 1 to determine the cumulative percentage of drug release. The results are shown in FIG. 8.

Formulations 11 and 12, which contain cholesterol as the hardly water-soluble substance and further contain NaCl as the water-soluble additive agent, attained an excellent sustained-release for a long period, namely 2 months.

TABLE 8

| | Sheet thickness | Vinaxanthone | Cholesterol | Other additive agents |
| --- | --- | --- | --- | --- |
| Formulation 11 | 0.3 mm | 10 wt % | 12 wt % | NaCl 8 wt % |
| Formulation 12 | 0.3 mm | 10 wt % | 15 wt % | NaCl 5 wt % |

Example 13

Crystalline sodium chloride was milled in a mortar to adjust the particle diameter thereof to 100 μm or less. To the above-obtained sodium chloride (10 mg) were added L-HPC (50 mg) and then powder vinaxanthone (20 mg), and the three kinds of powder were mixed all together in a mortar to give a mixed powder. SILASTIC Q7-4750 Silicone A component (85 mg) and Silicone B component (85 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.5 mm. The sheet formulation was cut to give Formulation 13.

Example 14

Crystalline sodium chloride was milled in a mortar to adjust the particle diameter thereof to 100 μm or less. To the above-obtained sodium chloride (15 mg) were added L-HPC (45 mg) and then powder vinaxanthone (20 mg), and the three kinds of powder were mixed all together in a mortar to give a mixed powder. SILASTIC Q7-4750 Silicone A component (85 mg) and Silicone B component (85 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.5 mm. The sheet formulation was cut to give Formulation 14.

Test Example 9

Figure 9:
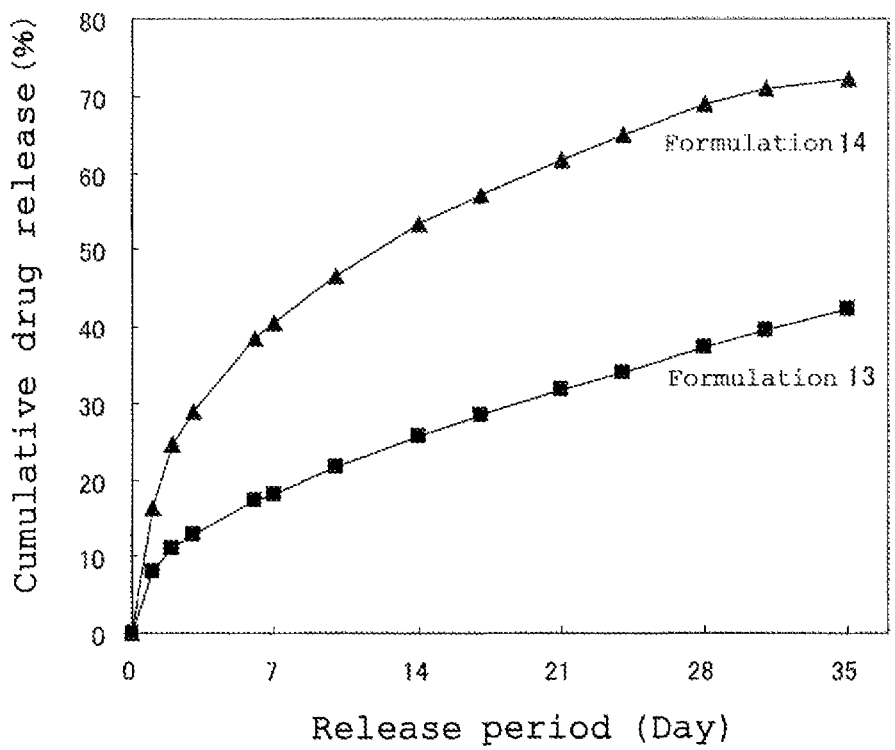
FIG. 9 Results of Test Example 9 are shown.

Each of the formulations prepared in Examples 13 and 14 (see, Table 9) was tested in the same manner as Test Example 1 to determine the cumulative percentage of drug release. The results are shown in FIG. 9.

Formulations 13 and 14, which have a thickness of 0.5 mm and contain L-HPC as the hardly water-soluble additive agent and NaCl as the water-soluble additive agent, attained an excellent sustained-release for a long period, namely 1 month or more.

TABLE 9

| | Sheet thickness | Vinaxanthone | L-HPC | Other additive agents |
| --- | --- | --- | --- | --- |
| Formulation 13 | 0.5 mm | 8 wt % | 20 wt % | NaCl 4 wt % |
| Formulation 14 | 0.5 mm | 8 wt % | 18 wt % | NaCl 6 wt % |

Example 15

Crystalline sodium chloride was milled in a mortar to adjust the particle diameter thereof to 100 μm or less. To the above-obtained sodium chloride (15 mg) were added L-HPC (85 mg) and then powder vinaxanthone (50 mg), and the three kinds of powder were mixed all together in a mortar to give a mixed powder. SILASTIC Q7-4750 Silicone A component (175 mg) and Silicone B component (175 mg) manufactured by Dow Corning were kneaded together with a twin roll. After the above silicones were kneaded, all of the above-obtained mixed powder was quickly added thereto, and the mixture was kneaded. The kneaded product was set into a compact Ram-type extruder, extruded through a die having a diameter of 0.3 mm, and then cured at 40° C. for 1 day to give a rod formulation with a diameter of 0.35 mm. The rod formulation was cut to give Formulation 15.

Test Example 10

Figure 10:
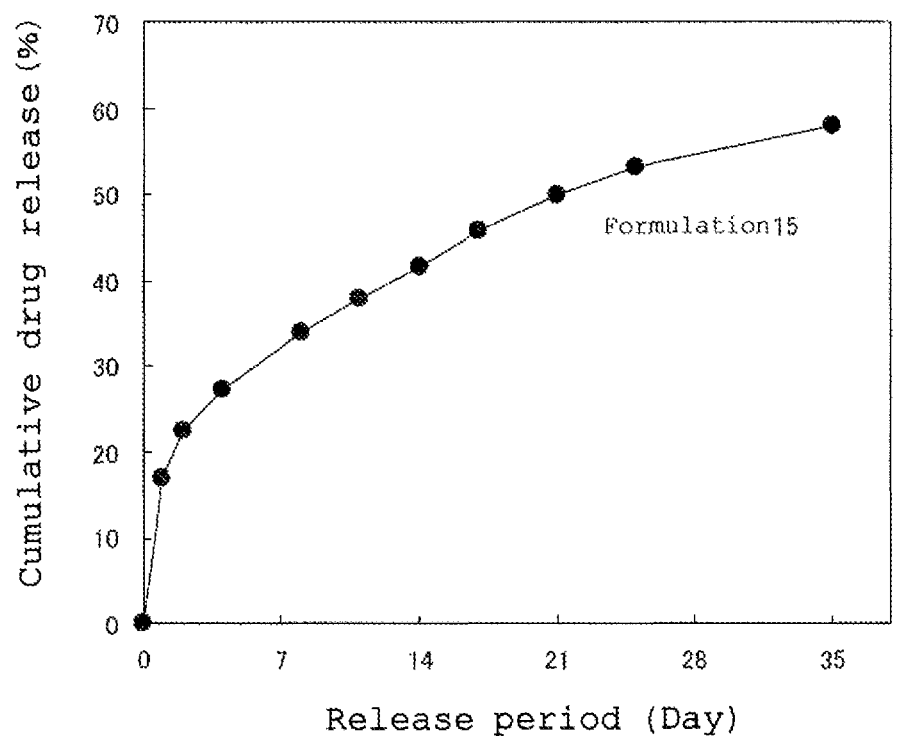
FIG. 10 Results of Test Example 10 are shown.

Formulation 15 prepared in Example 15 was cut into a length of 7 mm, kept at 37° C. in PBS (1 mL), measured the vinaxanthone released from the formulation with a high performance liquid chromatograph, and the value was calculated to determine the cumulative percentage of drug release. The results are shown in FIG. 10.

The present formulation, which is a rod-like formulation with a diameter of 0.35 mm containing L-HPC as the hardly water-soluble additive agent and NaCl as the water-soluble additive agent, attained an excellent sustained-release for a long period, namely 1 month or more.

TABLE 10

| | Rod diameter | Vinaxanthone | L-HPC | Other additive agents |
| --- | --- | --- | --- | --- |
| Formulation 15 | φ 0.35 mm | 10 wt % | 17 wt % | NaCl 3 wt % |

TABLE 10-continued

| | Rod diameter | Vinaxanthone | L-HPC | Other additive agents |
|---|---|---|---|---|

Comparative Example 1

SILASTIC Q7-4750 Silicone A component (147 mg) and Silicone B component (147 mg) manufactured by Dow Corning were kneaded together with a twin roll. After the above silicones were kneaded, powder vinaxanthone (6 mg) was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 1.

Test Example 11

Figure 11:
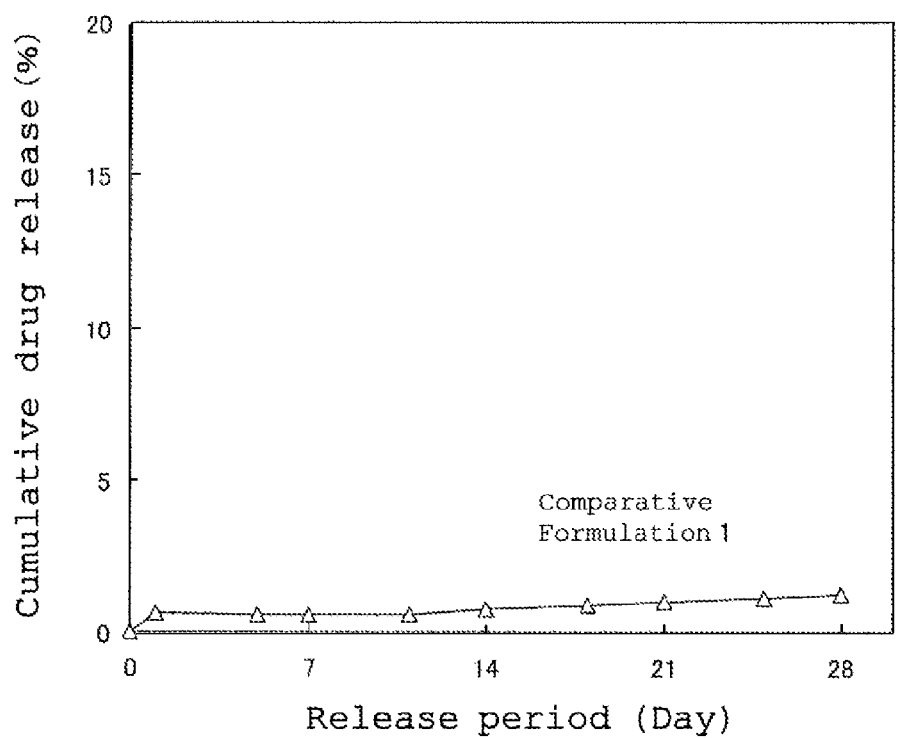
FIG. 11 Results of Test Example 11 are shown.

Comparative Formulation 1 prepared in Comparative Example 1 was tested in the same manner as Test Example 1 to determine the cumulative percentage of drug release. The results are shown in FIG. 11.

The comparative formulation, which contains 2% of vinaxanthone without any additive agents, released only a few amount of vinaxanthone over 4 weeks and most of the vinaxanthone remained inside the formulation.

TABLE 11

| | Sheet thickness | Vinaxanthone | Other additive agents | |
|---|---|---|---|---|
| Comparative Formulation 1 | 0.3 mm | 2 wt % | None | Decrease of release |

Comparative Example 2

Water-soluble HPC containing hydroxypropoxyl group in an amount of 53% or more (75 mg) and powder vinaxanthone (5 mg) were mixed in a mortar to give a mixed powder. SILASTIC Q7-4750 Silicone A component (85 mg) and Silicone B component (85 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 2.

Test Example 12

Figure 12:
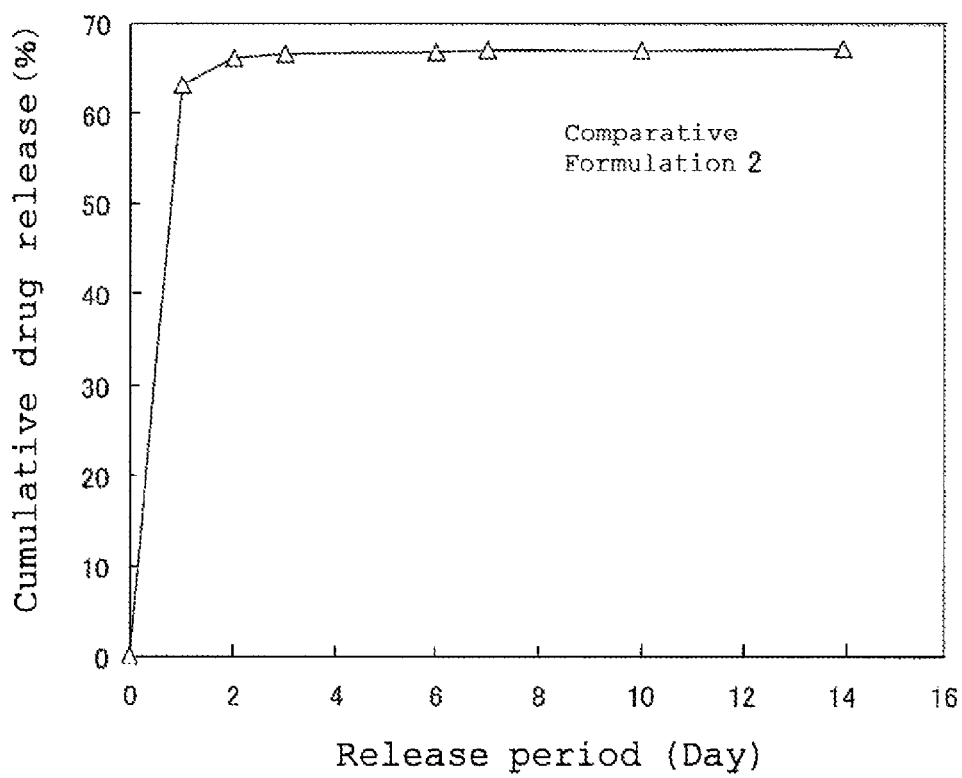
FIG. 12 Results of Test Example 12 are shown.

Comparative Formulation 2 prepared in Comparative Example 2 was tested in the same manner as Test Example 1 to determine the cumulative percentage of drug release. The results are shown in FIG. 12.

The comparative formulation, which contains 2% of vinaxanthone and contains a water-soluble HPC having 53% or more of hydroxypropoxyl group as an additive agent, released 60% or more of the drug by the initial burst on Day 1 and after that, no sustained-release were observed.

In contrast, the additive agent of the present invention contained in Formulation 1 is a low substituted HPC which is a hardly water-soluble additive-agent containing 5 to 16% of hydroxypropoxyl group, and Formulation 1 attained a small initial-burst with a sustained-release for 1 month (see, Test Example 1, FIG. 1).

TABLE 12

| | Sheet thickness | Vinaxanthone | Additive agents | |
|---|---|---|---|---|
| Comparative Formulation 2 | 0.3 mm | 2 wt % | HPC (containing 53.4% to 77.5% of hydroxypropoxyl group) 30 wt % | Water-soluble additive agent, initial burst |

Comparative Example 3

Crystalline sodium chloride was milled in a mortar to adjust the particle diameter thereof to 100 μm or less. To the above-obtained sodium chloride (90 mg) was added powder vinaxanthone (6 mg), and the two kinds of powder were mixed all together in a mortar to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 3.

Comparative Example 4

Glucose (90 mg) and powder vinaxanthone (6 mg) were mixed in a mortar to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 4.

Comparative Example 5

D-mannitol (90 mg) and powder vinaxanthone (6 mg) were mixed in a mortar to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 5.

Comparative Example 6

PEG4000 (90 mg) and powder vinaxanthone (6 mg) were mixed in a mortar to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 6.

Test Example 13

Figure 13:
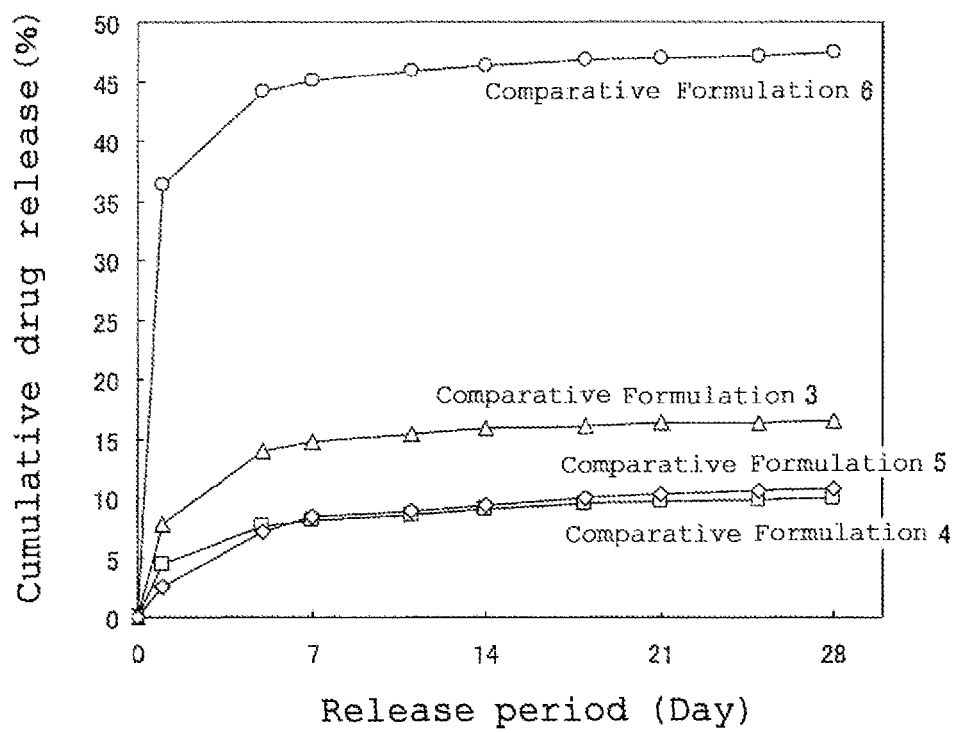
FIG. 13 Results of Test Example 13 are shown.

Each of the comparative formulations prepared in Comparative Examples 3 to 6 (see, Table 13) was tested in the same manner as Test Example 1 to determine the cumulative percentage of drug release. The results are shown in FIG. 13.

These comparative formulations do not contain hardly water-soluble additive agents, but instead each of them contains a different water-soluble substance as an additive agent. Comparative Formulation 6, which contains PEG4000, had a large initial-burst. The other comparative formulations had a comparatively small initial-burst, however, showed a drug release for only a short period. Thus all of the comparative formulations could not attain a sustained-release for a long period which is required for the treatment of spinal cord injury.

TABLE 13

| | Sheet thickness | Vinaxanthone | Additive agents | |
|---|---|---|---|---|
| Comparative Formulation 3 | 0.3 mm | 2 wt % | NaCl 30 wt % | Water-soluble additive agent, no sustained-release |
| Comparative Formulation 4 | 0.3 mm | 2 wt % | Glucose 30 wt % | |
| Comparative Formulation 5 | 0.3 mm | 2 wt % | D-mannitol 30 wt % | |
| Comparative Formulation 6 | 0.3 mm | 2 wt % | PEG4000 30 wt % | |

Comparative Example 7

CMC-Na (carboxymethylcellulose-sodium) (90 mg) and powder vinaxanthone (6 mg) were mixed in a mortar to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 7.

Comparative Example 8

Crystalline sodium chloride was milled in a mortar to adjust the particle diameter thereof to 100 μm or less. To the above-obtained sodium chloride (15 mg) were added CMC-Na (75 mg) and then powder vinaxanthone (6 mg), and the three kinds of powder were mixed all together in a mortar to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 8.

Comparative Example 9

To lactose (45 mg) were added CMC-Na (45 mg) and then powder vinaxanthone (6 mg), and the three kinds of powder were mixed all together in a mortar to give a mixed powder. SILASTIC Q7-4750 Silicone A component (102 mg) and Silicone B component (102 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 9.

Test Example 14

Figure 14:
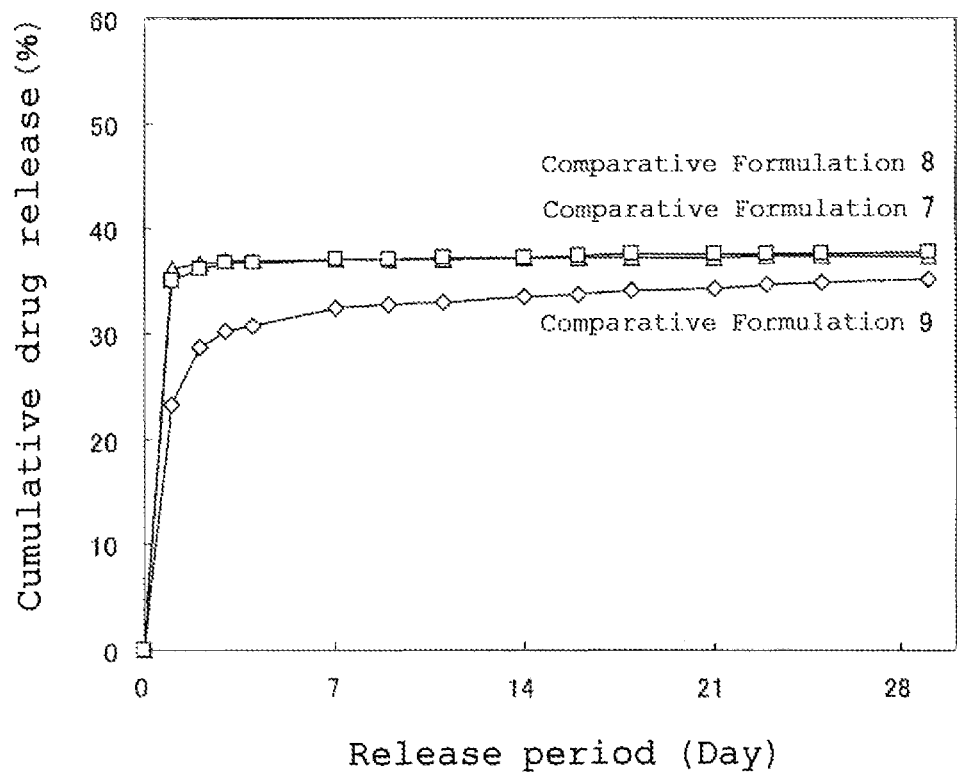
FIG. 14 Results of Test Example 14 are shown.

Each of the comparative formulations prepared in Comparative Examples 7 to 9 (see, Table 14) was tested in the same manner as Test Example 1 to determine the cumulative percentage of drug release. The results are shown in FIG. 14.

These comparative formulations do not contain hardly water-soluble substance, but contain CMC-Na as a water-soluble additive agent. As clearly shown in FIG. 14, all of them showed an initial burst, but no sustained-release were observed.

TABLE 14

| | Sheet thickness | Vinaxanthone | Additive agents | |
|---|---|---|---|---|
| Comparative Formulation 7 | 0.3 mm | 2 wt % | CMC-Na 30 wt % | Water-soluble additive agent, initial burst, no sustained-release |
| Comparative Formulation 8 | 0.3 mm | 2 wt % | CMC-Na 25 wt % + NaCl 5 wt % | |
| Comparative Formulation 9 | 0.3 mm | 2 wt % | CMC-Na 15 wt % + lactose 15 wt % | |

Comparative Example 10

Crystalline sodium chloride was milled in a mortar to adjust the particle diameter thereof to 100 μm or less. To the above-obtained sodium chloride (6 mg) were added sodium desoxycholate (34 mg) and then powder vinaxanthone (20 mg), and the three kinds of powder were mixed all together in a mortar to give a mixed powder. SILASTIC Q7-4750 Silicone A component (70 mg) and Silicone B component (70 mg) manufactured by Dow Corning were kneaded together with a twin roll. After the above silicones were kneaded, all of the above-obtained mixed powder was quickly added thereto, and the mixture was kneaded. Then, the kneaded product was rolled into a sheet shape with a twin roll and cured at 40° C. for 1 day to give a sheet formulation with a thickness of 0.3 mm. The sheet formulation was cut to give Comparative Formulation 10.

Test Example 15

Figure 15:
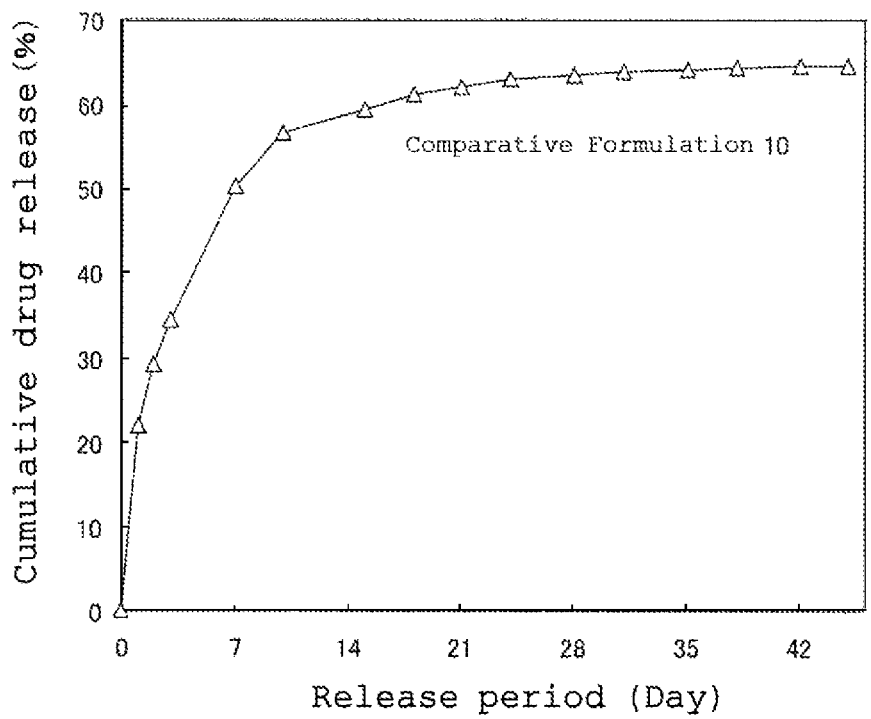
FIG. 15 Results of Test Example 15 are shown.

Comparative Formulation 10 prepared in Comparative Example 10 was tested in the same manner as Test Example 1 to determine the cumulative percentage of drug release. The results are shown in FIG. 15.

The comparative formulation, which does not contain any hardly water-soluble substances but contain sodium desoxycholate (DC) and NaCl as water-soluble additive agents, showed a release for a short period of about 1 week and could not attain a sustained-release for a long period which is required for the treatment of spinal cord injury.

TABLE 15

| | Sheet thickness | Vinaxanthone | Additive agents | |
|---|---|---|---|---|
| Comparative Formulation 10 | 0.3 mm | 10 wt % | DC 17 wt % + NaCl 3 wt % | Water-soluble additive agent, unsustainable |

Thus, the above-shown Examples and Comparative Examples demonstrate the effects of the present invention. In particular, the treatment of spinal cord injury needs to continuously deliver the semaphorin inhibitor for at least 2 weeks or more, desirably 1 month or more; and the above-shown Examples and Comparative Examples demonstrate that the present formulation can be used accordingly.

The following illustrates some tests carried out in animals treated with the present formulation to evaluate the therapeutic effects on spinal cord injury and the toxicity in the vicinity of the nerve tissue, which is an important factor for an agent for local treatment.

Test Example 16

Figure 16:
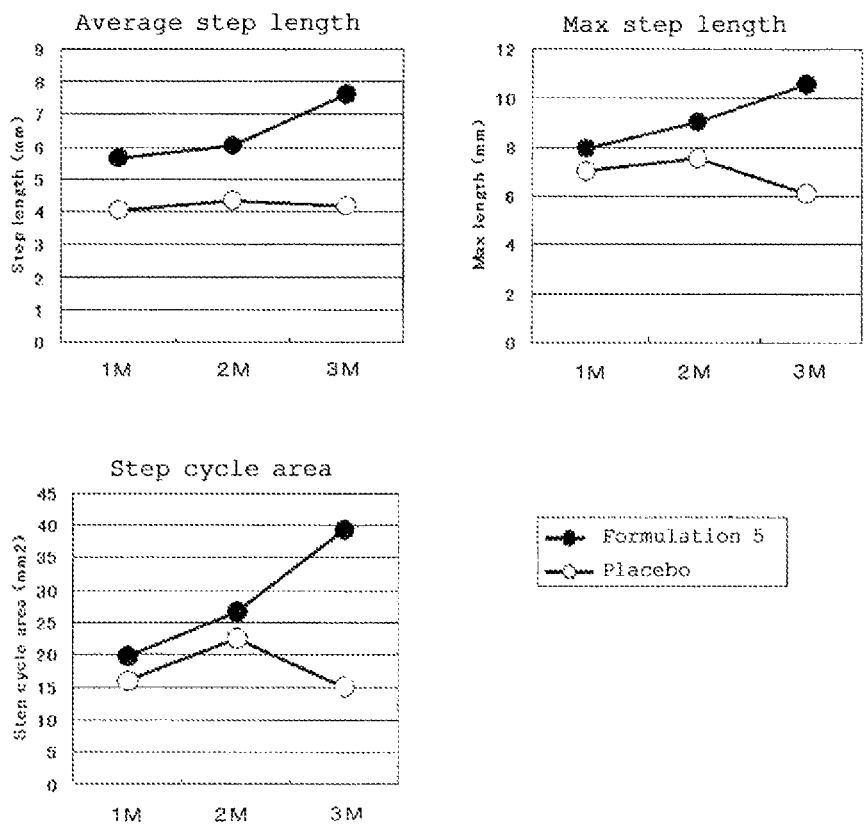
FIG. 16 Results of Test Example 16 are shown.

Recovery Effects of Motor Function in Complete Spinal Cord Transection Model in Rats Spinal cord of a female Sprague Dawley rat (body weight: 200 g to 250 g) was completely transected at the $12^{th}$ thoracic vertebra (T12) with ophthalmological scissors. Formulation 5 (which is a sheet-like formulation with a thickness of 0.3 mm) was cut into a size of 3 mm×3 mm and placed subarachnoidally in the transection site. As a control, a placebo sheet without containing vinaxanthone (i.e. a formulation containing the same contents as Formulation 5 except vinaxanthone) (L-HPC 17%, sodium chloride 3%, silicone 80%) was cut into the same size and placed. A kinematic analysis of the hind limbs was carried out 1, 2 and 3 months after the surgery. The results are shown in FIG. 16. A marked recovery of average step length, max length and step cycle area was observed in the group administered Formulation 5 compared with the placebo group. The results strongly demonstrate that the administration of the vinaxanthone-containing formulation of the present invention is an effective method for treating spinal cord injury. In addition, the numbers of animals used in the drug-administered group and placebo group were 4 rats and 5 rats, respectively.

Test Example 17

Toxicity to Nerve Tissue

In applying the semaphorin inhibitor to spinal cord injury, the silicone sheet containing the drug is placed in the injured site. In this case, there are concerns that the concentration around the surface where the drug is placed may be kept too high for a long period and also the contact of the formulation may have physical effects on the tissue surface of the placed site. In order to evaluate them, the formulation was placed in the subdural space of a rat with spinal cord injury, and after that the surface of the spinal cord was investigated.

Figure 17:
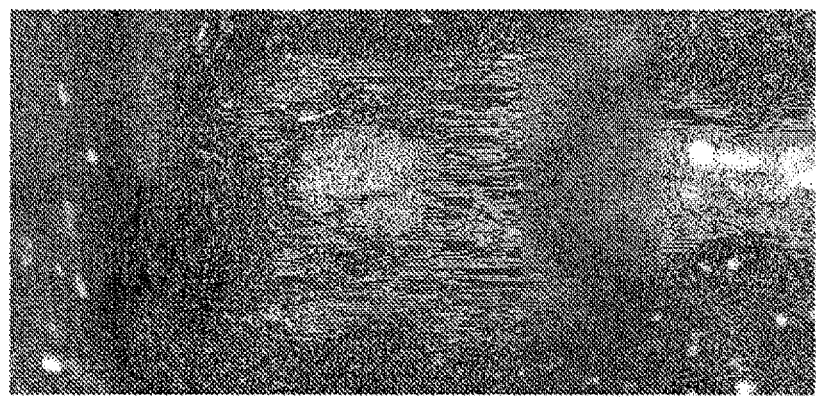
FIG. 17 Rat's dura mater of the spinal cord exposed at T8 (the $8^{th}$ thoracic vertebra) in Test Example 17 is shown.
Figure 18:
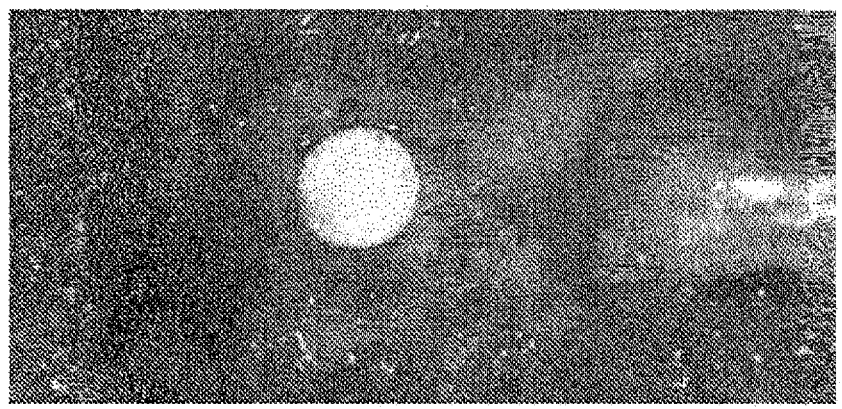
FIG. 18 Spinal cord in Test Example 17 wherein the sheet is inserted is shown.
Figure 19:
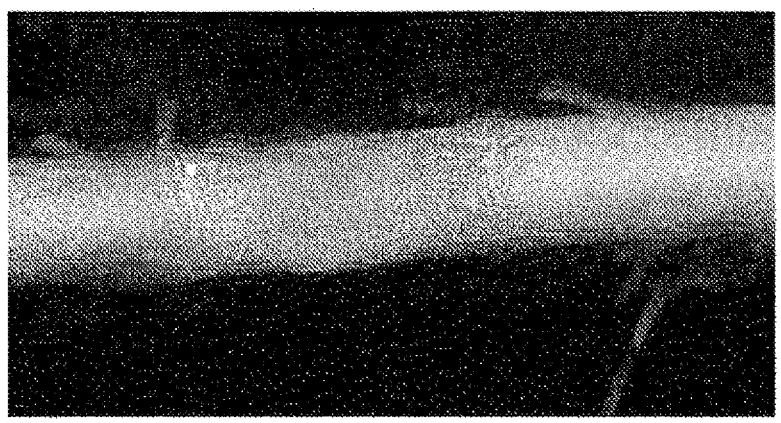
FIG. 19 Spinal cord treated with placebo observed at the end of Test Example 17 is shown.
Figure 20:
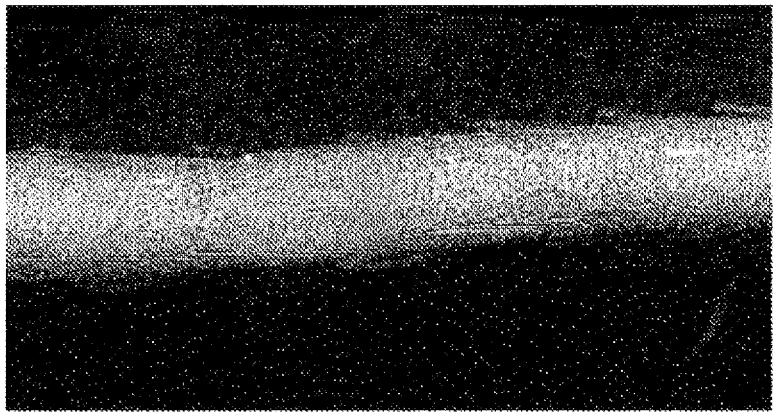
FIG. 20 Spinal cord treated with Formulation 5 observed at the end of Test Example 17 is shown.
Figure 21:
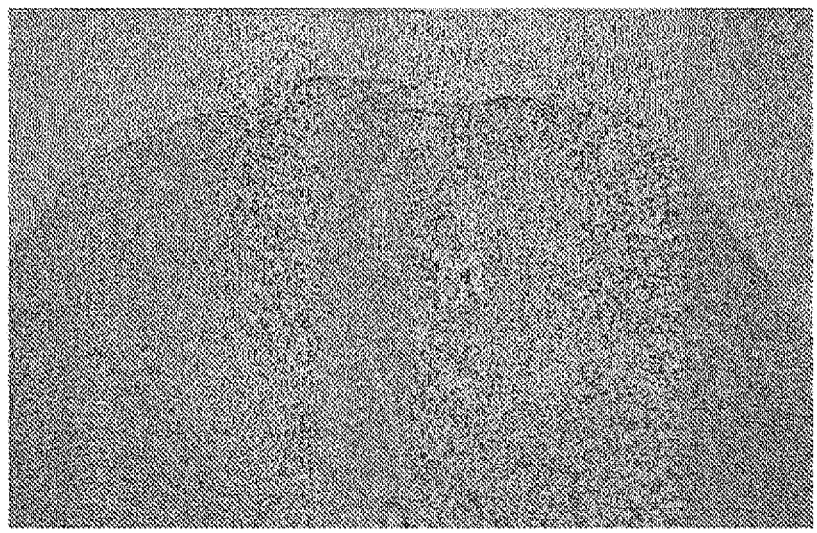
FIG. 21 A microscopic photograph of a cross-section of the spinal cord treated with Formulation 5 observed at the end of Test Example 17 is shown.

The drugs tested herein were Formulation 5 and a placebo sheet (i.e. a formulation containing the same contents as Formulation 5 except vinaxanthone) (L-HPC 17%, sodium chloride 3%, silicone 80%) as a control, wherein both of them were punched to a diameter of 2 mm. The dura mater at T8 of the spinal cord in the rat was sectioned (see, FIG. 17), and the testing sheet, which had been dipped in PBS for 2 days beforehand to stabilize the drug release, was inserted subdurally (see, FIG. 18) and moved to around T7. 4 Days after, the rat was perfusion-fixed and the spinal cord was withdrawn to observe the spinal cord tissue located immediately below the sheet with a microscope. The results show that there is no abnormal finding in the spinal cord surface of either placebo (see, FIG. 19) or Formulation 5 (see, FIG. 20). Furthermore, a histopathological examination of the rat administered Formulation 5 was carried out, and no degenerated changes were observed in the dorsal portions of the spinal cord (see, FIG. 21). Thus, the results demonstrate that the risk of inducing direct adverse-reactions by the administration of the vinaxanthone-containing formulation of the present invention is low.

Test Example 18

Figure 22:
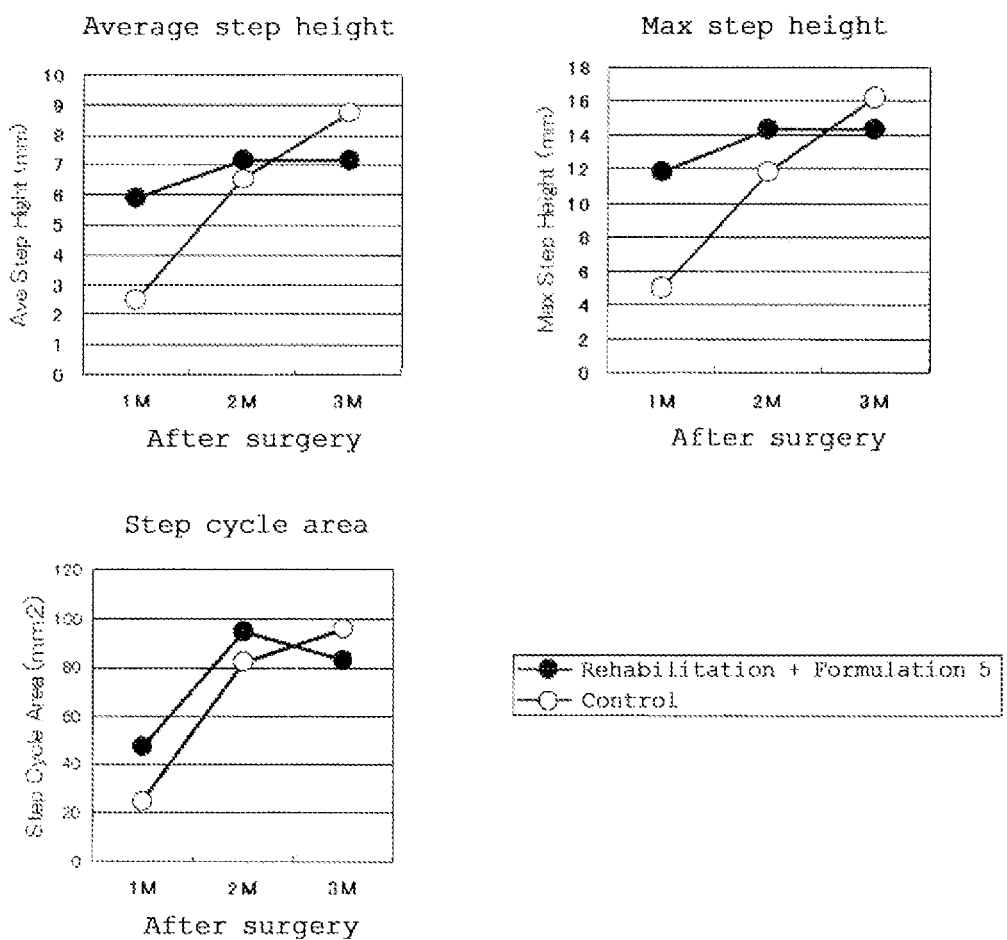
FIG. 22 Results of Test Example 18 are shown.

Effects of Silicone-Formulation Containing Semaphorin Inhibitory Drug on Rehabilitation in a Spinal Cord Injury Model in Rats Formulation 5 (which is a sheet-like formulation with a thickness of 0.3 mm) cut into a size of 3 mm×3 mm was used to study the effects of the semaphorin inhibitor (i.e. vinaxanthone) on a rehabilitation therapy in a spinal cord injury model. In the same manner as Test Example 16, the spinal injury model in rats was prepared, and Formulation 5 was placed in some rats while placebo sheet was placed in the other rats as a control group. From 1 week after the surgery, the treated rats were rehabilitated with a treadmill for 3 months. The treadmill rehabilitation is the same as the therapy actually applied to patients with spinal cord injury. A kinematic analysis of the hind limbs was carried out 1, 2 and 3 months after the surgery. The results are shown in FIG. 22. In the group treated with only rehabilitation, a recovery of average step length, max length and step cycle area was observed 2 to 3 months after the surgery. However, in the group wherein administration of Formulation 5 was combined with rehabilitation, a marked recovery of average step length, max length and step cycle area was observed much earlier, i.e. 1 month after the surgery. The results demonstrate that the administration of the vinaxanthone-containing formulation of the present invention shortens the period required to exhibit the effect of rehabilitation in treating spinal cord injury. In addition, the numbers of animals used in the drug-administered group and placebo group were 4 rats and 2 rats, respectively.

Test Example 19

Figure 23:
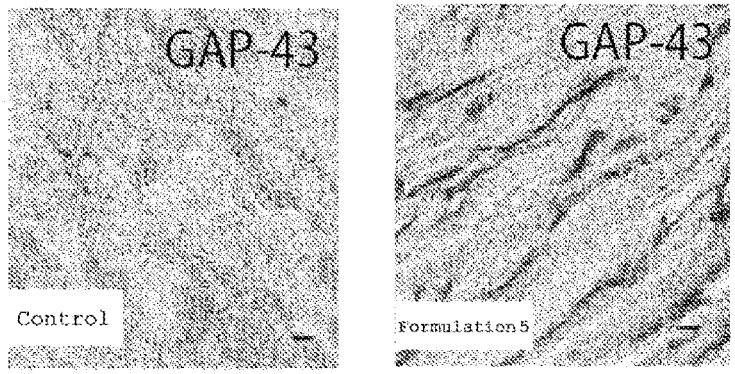
FIG. 23 Photographs of the immunohistochemistry of the spinal cord in Test Example 19 are shown.
Figure 23:
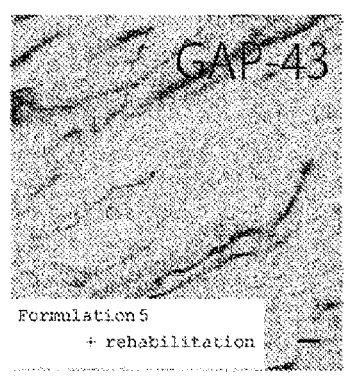
Figure 24:
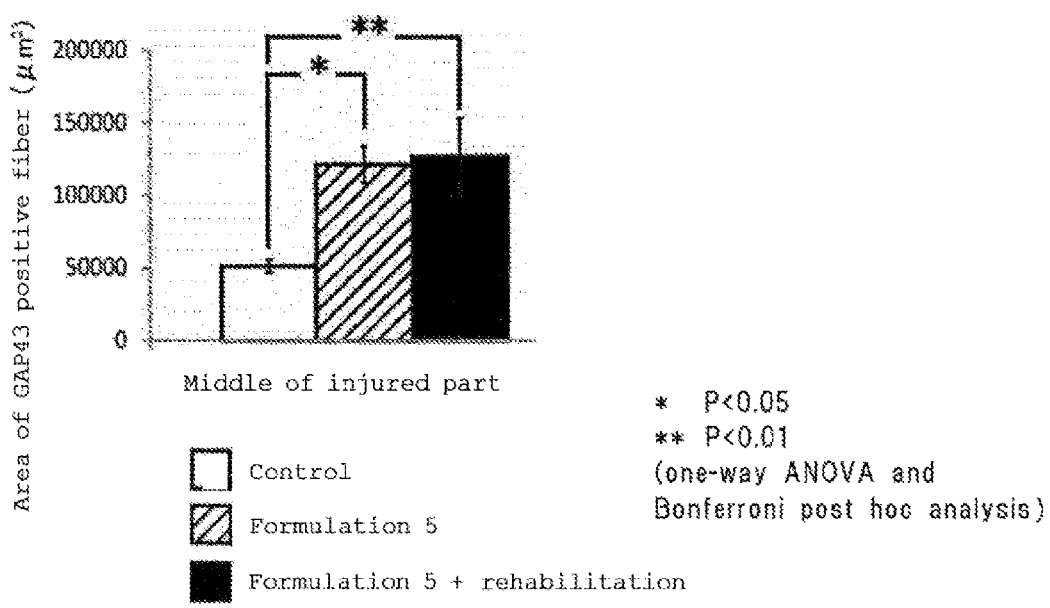
FIG. 24 Results of Test Example 19 are shown.
Figure 25:
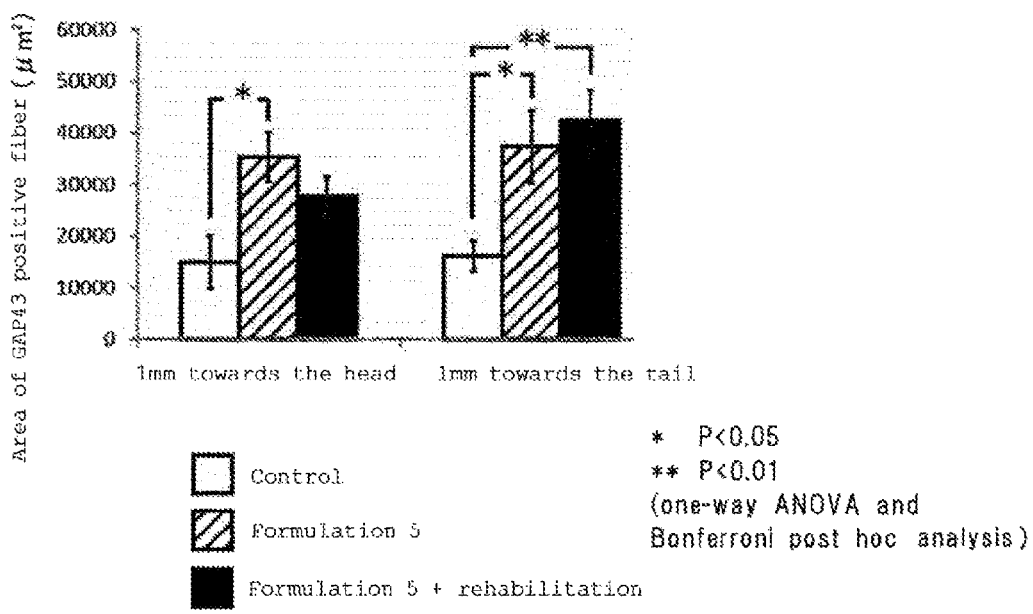
FIG. 25 Results of quantification from the immunohistochemistry in Test Example 19 are shown.

Effects of Silicone Formulation Containing Semaphorin Inhibitory Drug on Re-Elongation of Spinal Nerve The test was carried out to evaluate whether or not the silicone formulation containing semaphorin-inhibitory drug has a re-elongation effect on nerve fibers in the injured spinal cord. In the same manner as Test Examples 16 and 18, the rat spinal injured model was prepared, and Formulation 5 was placed in some rats, while placebo sheet was placed in the other rats as a control group. Among the rats administered Formulation 5, some of them were rehabilitated for 3 months like Test Example 18. 3 months after the surgery, the rat was perfusion-fixed and the spinal cord was withdrawn. A frozen section of the spinal cord was prepared, and the section was developed immunohistochemically with an antibody against GAP43 which is a marker of regenerating nerve fibers. The transected site was observed with a microscope. As shown in FIG. 23, GAP43 positive fiber of the rat administered only the drug (Formulation 5) and the rat administered the drug and also treated with rehabilitation (Formulation 5+rehabilitation) was increased compared with that of the control group. The amount of GAP43 positive fiber was quantified by image analysis with a computer, and the drug-administered group showed a significant increase in both the injured part (see, FIG. 24) and the part 1 mm away from the injured part towards the head or tail (see, FIG. 25). The results demonstrate that the silicone-sheet-formulation containing semaphorin inhibitory drug has a re-elongation effect on the nerve fibers in the injured spinal cord.

Figure 26:
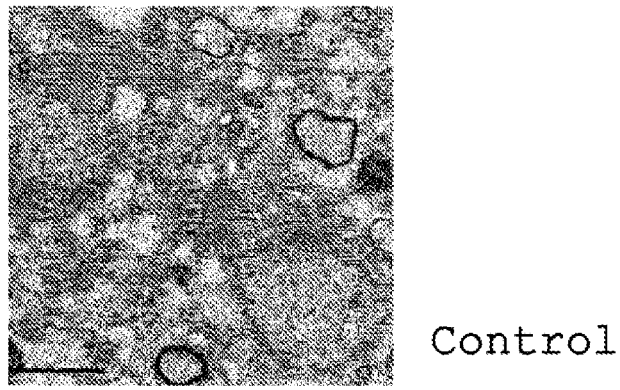
FIG. 26 Electron microscopic photographs of the spinal cord in Test Example 19 are shown.
Figure 26:
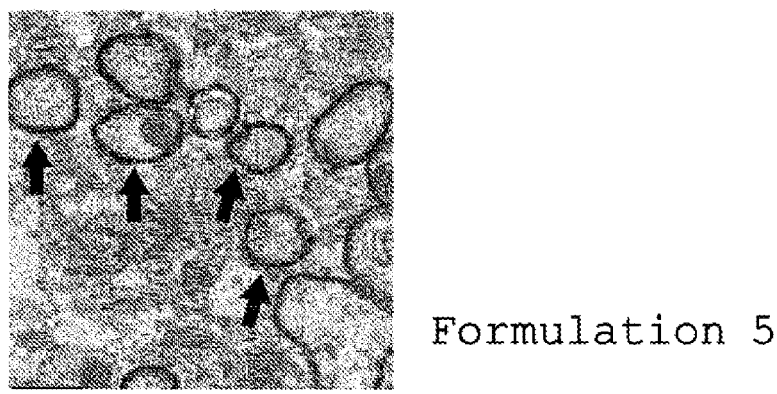

Furthermore, the re-elongated nerve fibers of the control group and those of the group administered Formulation 5 were observed with an electron microscope. As shown in FIG. 26, only a few nerve fibers have myelin sheath in the control group, whereas a great many nerve fibers have myelin sheath in the group administered Formulation 5 (shown by arrows in FIG. 26). The results demonstrate that maturation is also accelerated in the nerve fibers which were re-elongated by the semaphorin-inhibitory silicone-sheet.

In addition, the numbers of animals used in the control group, drug-administered group, and drug-administered group combined with rehabilitation were all 11 rats.

Test Example 20

Figure 27:
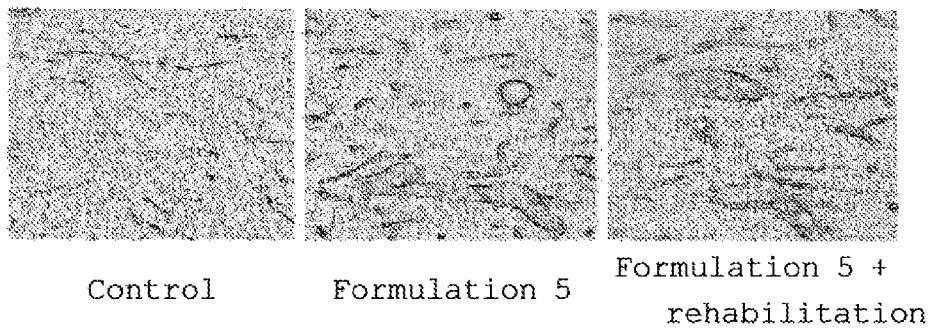
FIG. 27 Photographs of the immunohistochemistry of the spinal cord in Test Example 20 are shown.
Figure 28:
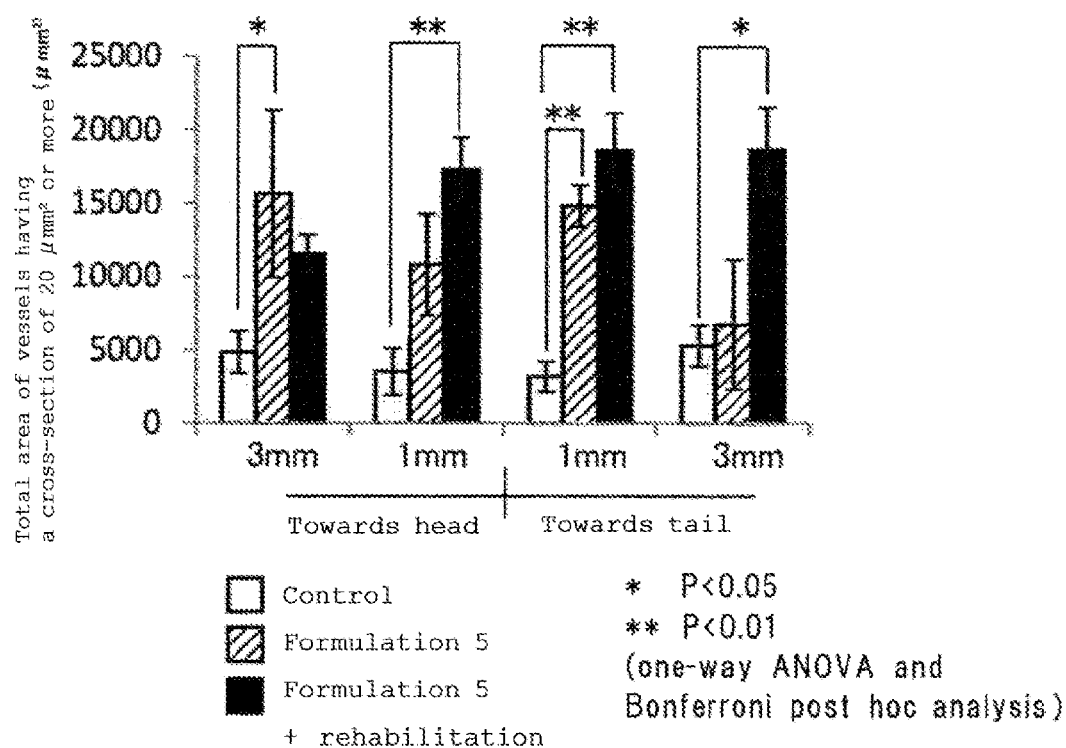
FIG. 28 Results of quantification from the immunohistochemistry in Test Example 20 are shown.

Effects of the Silicone-Sheet-Formulation Containing Semaphorin Inhibitory Drug on Enhancing Angiogenesis It is important to regenerate the blood vessel after spinal cord injury for the recovery of the injured tissue. The test was carried out to evaluate whether or not the silicone-sheet-formulation containing semaphorin inhibitory drug enhances angiogenesis in the spinal cord after the injury. The frozen section prepared in Test Example 19 was developed immunohistochemically with an antibody against RECA-1 which is a marker of vascular endothelial cell. The part which is 1 mm away from the transected site towards the tail was observed with a microscope. As shown in FIG. 27, RECA-1 positive cell of the rat administered only the drug (Formulation 5) and the rat administered the drug and also treated with rehabilitation (Formulation 5+rehabilitation) was increased compared with that of the control group. The diameter of neovessel is larger than that of mature vessel, and thus the number of vessels having an area of 20 $\mu m^2$ or more was counted with a computer. The drug-administered group showed a significant increase in all of the following 4 parts: 1 or 3 mm away from the injured part towards the head or tail (see, FIG. 28). The results demonstrate that the semaphorin-inhibitory silicone-sheet-formulation enhances angiogenesis in the spinal cord after the injury.

Test Example 21

Figure 29:
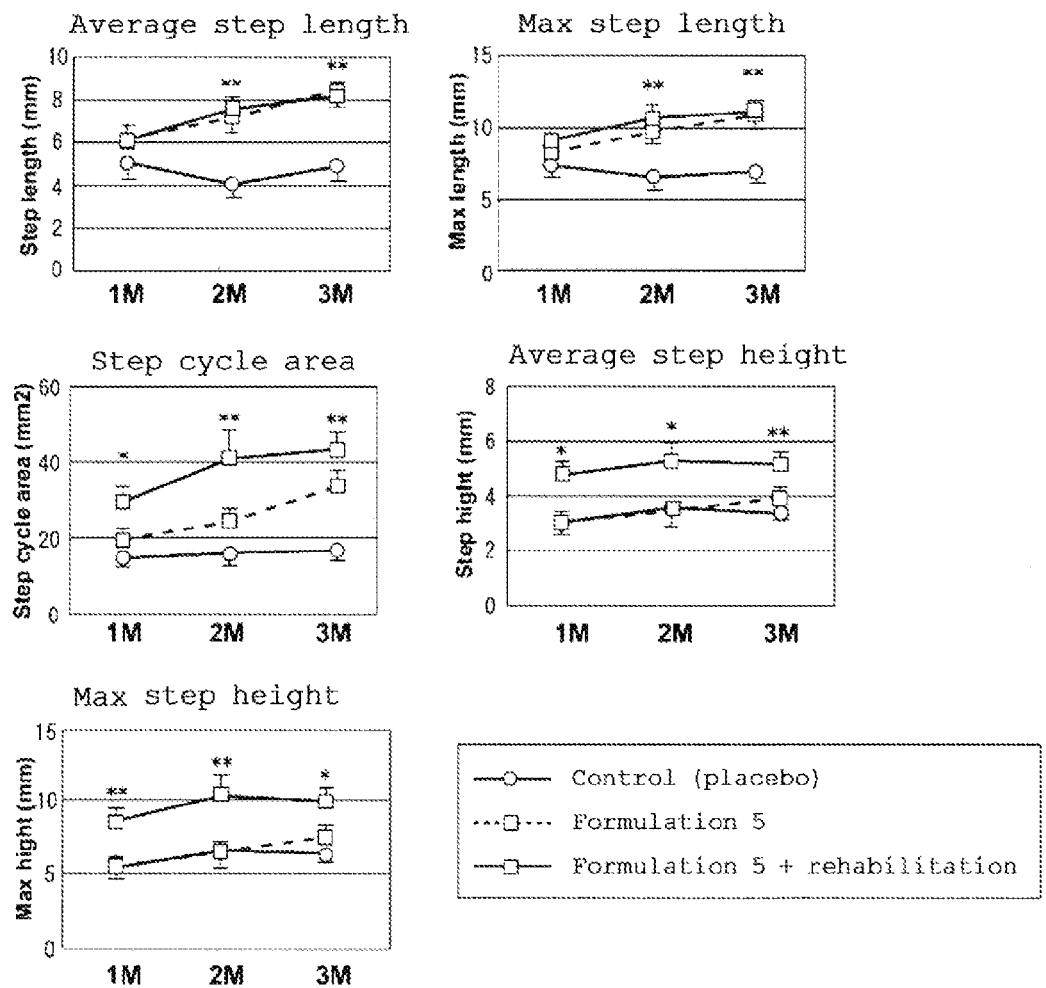
FIG. 29 Results of Test Example 21 are shown.

Effect of Enhancing Action of the Silicone-Sheet-Formulation Containing Semaphorin Inhibitory Drug by Combining Rehabilitation Evaluated in Rat Model with Spinal Cord Injury Formulation 5 (which is a sheet-like formulation with a thickness of 0.3 mm) was cut into a size of 3 mm×3 mm. The test was carried out to study the effects of rehabilitation on the action of the semaphorin inhibitor (i.e. vinaxanthone), wherein the relationship between the rehabilitation and vinaxanthone is opposite to Test Example 18. In the same manner as Test Example 16, spinal cord injury model in rats was prepared, and Formulation 5 was placed in some rats, while placebo sheet was placed in the other rats as a control group. The group administered Formulation 5 was further divided into 2 groups; and from 1 week after the surgery, one of the groups was rehabilitated with a treadmill for 3 months. A kinematic analysis of the hind limbs was carried out 1, 2 and 3 months after the surgery. The results are shown in FIG. 29. The results show that the recovery of average step length, max step length, and step cycle area was enhanced by combining Formulation 5. In particular, the results show that the recovery in step cycle area of the group treated with rehabilitation and Formulation 5 was markedly enhanced compared with that of the control group and also the group treated with only Formulation 5. In addition, the results show that the recovery in average step height and max step height of the group treated with only Formulation 5 was not clearly observed, but that of the group treated with rehabilitation and Formulation 5 was markedly enhanced. Thus, the results demonstrate that effect of the vinaxanthone-containing formulation of the present invention can be enhanced by combining the administration thereof with rehabilitation. In addition, the number of animals used in the control group, drug-administered group and drug-administered group combined with rehabilitation were 11 rats, 13 rats and 11 rats, respectively.

Example 16

Crystalline sodium chloride is milled in a mortar to adjust the particle diameter thereof to 100 μm or less. To the above-obtained sodium chloride (50 mg) are added partly pregelatinized starch (170 mg) and then powder vinaxanthone (100 mg), and the three kinds of powder are mixed all together in the mortar to give a mixed powder. SILASTIC Q7-4750 Silicone A component (340 mg) and Silicone B component (340 mg) manufactured by Dow Corning are kneaded together with a twin roll. After the above silicones are kneaded, all of the above-obtained mixed powder is quickly added thereto, and the mixture is kneaded. Then, the kneaded product is rolled into a sheet shape with a twin roll and cured at 40° C. for 1 day to give a sheet formulation with a thickness of 0.3 mm. The sheet formulation is cut into a size of 5 mm×7 mm to give Formulation 16.

Example 17

Crystalline sodium chloride is milled in a mortar to adjust the particle diameter thereof to 100 μm or less. To the above-obtained sodium chloride (30 mg) are added croscarmellose sodium (70 mg) and then powder vinaxanthone (100 mg), and the three kinds of powder are mixed all together in the mortar to give a mixed powder. SILASTIC Q7-4750 Silicone A component (400 mg) and Silicone B component (400 mg)

manufactured by Dow Corning are kneaded together with a twin roll. After the above silicones are kneaded, all of the above-obtained mixed powder is quickly added thereto, and the mixture is kneaded. Then, the kneaded product is rolled into a sheet shape with a twin roll and cured at 40° C. for 1 day to give a sheet formulation with a thickness of 0.3 mm. The sheet formulation is cut into a size of 5 mm×7 mm to give Formulation 17.

Example 18

Crystalline sodium chloride is milled in a mortar to adjust the particle diameter thereof to 100 μm or less. To the above-obtained sodium chloride (30 mg) are added crospovidone (120 mg) and then powder vinaxanthone (100 mg), and the three kinds of powder are mixed all together in the mortar to give a mixed powder. SILASTIC Q7-4750 Silicone A component (375 mg) and Silicone B component (375 mg) manufactured by Dow Corning are kneaded together with a twin roll. After the above silicones are kneaded, all of the above-obtained mixed powder is quickly added thereto, and the mixture is kneaded. Then, the kneaded product is rolled into a sheet shape with a twin roll and cured at 40° C. for 1 day to give a sheet formulation with a thickness of 0.3 mm. The sheet formulation is cut into a size of 5 mm×7 mm to give Formulation 18.

Test Example 22

Each of the formulations prepared in Examples 16 to 18 (see, Table 16) is tested in the same manner as Test Example 1 to determine the cumulative percentage of drug release.

TABLE 16

| | Sheet thickness | Vinaxanthone | Hardly water-soluble substance | Other additive agents |
|---|---|---|---|---|
| Formulation 16 | 0.3 mm | 10 wt % | Partly pregelatinized starch 17 wt % | NaCl 5 wt % |
| Formulation 17 | 0.3 mm | 10 wt % | CrosCMC-Na 7 wt % | NaCl 3 wt % |
| Formulation 18 | 0.3 mm | 10 wt % | Crospovidone 12 wt % | NaCl 3 wt % |

The invention claimed is:
1. A sustained-release formulation having a solid sheet or rod shape comprising:
a compound of Formula (1):

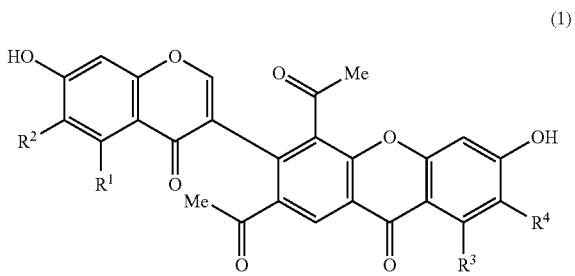

(1)

wherein $R^1$ is a hydrogen atom or a carboxyl group, $R^2$ is a hydrogen atom or a hydroxyl group, $R^3$ is a hydrogen atom or a carboxyl group, and $R^4$ is a hydrogen atom or a hydroxyl group, or a pharmaceutically acceptable salt thereof;
at least one water-insoluble or hardly water-soluble substance selected from the group consisting of a low substituted hydroxypropylcellulose, a partly pregelatinized starch, crospovidone, croscarmellose sodium, carmellose calcium, hydroxypropyl starch, myristic acid, lauric acid, palmitic acid, saccharin and cholesterol; and
a silicone biocompatible hydrophobic polymer.
2. The sustained-release formulation of claim 1, wherein the at least one water-insoluble or hardly water-soluble substance is low substituted hydroxypropylcellulose and/or cholesterol.
3. The sustained-release formulation of claim 1, wherein the solid sustained-release formulation has the solid sheet or rod shape and is suitable for placement in the vicinity of a spinal cord injury site or in a spinal cavity.
4. The sustained-release formulation of claim 1, wherein the solid sustained-release formulation has the sheet shape and a thickness of 0.1 to 1.5 mm.
5. The sustained-release formulation of claim 1, wherein the formulation comprises the water-insoluble or hardly water-soluble substance in 3 to 35% by weight per 100% by weight of the whole formulation.
6. The sustained-release formulation of claim 1, wherein the formulation comprises the silicone in 55% or more by weight per 100% by weight of the whole formulation.
7. The sustained-release formulation of claim 1, further comprising a water-soluble additive agent.
8. The sustained-release formulation of claim 7, wherein the water-soluble additive agent is at least one selected from the group consisting of sodium chloride, glucose, mannitol, lactose, glycine, sodium cholate, sodium glycocholate and sodium desoxycholate.
9. The sustained-release formulation of claim 7, wherein the water-soluble additive agent is at least one selected from the group consisting of sodium chloride and sodium desoxycholate.
10. The sustained-release formulation of claim 9, wherein the water-insoluble or hardly water-soluble substance is low substituted hydroxypropylcellulose, and the water-soluble additive agent is sodium chloride.
11. The sustained-release formulation of claim 9, wherein the hardly water-soluble substance is cholesterol, and the water-soluble additive agent is sodium desoxycholate.
12. The sustained-release formulation of claim 9 wherein the hardly water-soluble substance is cholesterol.
13. The sustained-release formulation of claim 1, comprising 10 to 40% by weight of
(i) the compound of Formula (1) or pharmaceutically acceptable salt thereof,
(ii) the at least one water-insoluble or hardly water-soluble substance, and
(iii) an optional water-soluble additive agent
per 100% by weight of the whole formulation,
provided that the total weight of the compound of Formula (1) or pharmaceutically acceptable salt thereof and the optional water-soluble additive agent is not more than 35% per 100% by weight of the whole formulation.
14. The sustained-release formulation of claim 1, wherein the compound of Formula (1) or pharmaceutically acceptable salt thereof is contained in an amount of 3 to 350 μg per 1 mg of the formulation.
15. The sustained-release formulation of claim 1, which is a matrix formulation.
16. The sustained-release formulation of claim 1, wherein $R^1$ and $R^3$ are each a carboxyl group, and $R^2$ and $R^4$ are each a hydroxyl group.

17. A sustained-release formulation having a solid sheet or rod shape consisting essentially of:
a compound of Formula (1):

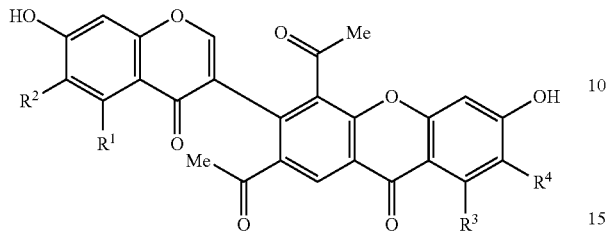

wherein $R^1$ is a hydrogen atom or a carboxyl group, $R^2$ is a hydrogen atom or a hydroxyl group, $R^3$ is a hydrogen atom or a carboxyl group, and $R^4$ is a hydrogen atom or a hydroxyl group, or
a pharmaceutically acceptable salt thereof;
at least one water-insoluble or hardly water-soluble substance selected from the group consisting of a low substituted hydroxypropylcellulose, a partly pregelatinized starch, crospovidone, croscarmellose sodium, carmellose calcium, hydroxypropyl starch, myristic acid, lauric acid, palmitic acid, saccharin and cholesterol;
a silicone biocompatible hydrophobic polymer; and
optionally a water-soluble additive agent.

\* \* \* \* \*